(12) United States Patent
You et al.

(10) Patent No.: US 11,058,874 B2
(45) Date of Patent: Jul. 13, 2021

(54) IONTOPHORESIS DEVICE, IONTOPHORESIS METHOD, AND SKIN CARE DEVICE INCLUDING SAME

(71) Applicant: AMOSENSE CO.,LTD, Chungcheongnam-do (KR)

(72) Inventors: Jin Young You, Incheon (KR); Dong Kun Lee, Seoul (KR); Sang Dong Jeong, Gimpo-si (KR); Dong Woo Kim, Cheonan-si (KR); Yeun Ho Bang, Gwangmyeong-si (KR)

(73) Assignee: Amosense Co., Ltd., Cheonan-si (KR)

( * ) Notice: Subject to any disclaimer, the term of this patent is extended or adjusted under 35 U.S.C. 154(b) by 212 days.

(21) Appl. No.: 16/308,104

(22) PCT Filed: Jun. 8, 2017

(86) PCT No.: PCT/KR2017/005973
§ 371 (c)(1),
(2) Date: Dec. 7, 2018

(87) PCT Pub. No.: WO2017/213442
PCT Pub. Date: Dec. 14, 2017

(65) Prior Publication Data
US 2019/0175907 A1    Jun. 13, 2019

(30) Foreign Application Priority Data

Jun. 8, 2016  (KR) .................. 10-2016-0071174
Jun. 8, 2016  (KR) .................. 10-2016-0071184
Jun. 8, 2016  (KR) .................. 10-2016-0071194

(51) Int. Cl.
*A61N 1/30*  (2006.01)
*A61N 1/32*  (2006.01)
(Continued)

(52) U.S. Cl.
CPC ............... *A61N 1/30* (2013.01); *A61N 1/044* (2013.01); *A61N 1/325* (2013.01); *A61N 5/0616* (2013.01);
(Continued)

(58) Field of Classification Search
CPC .......... A61N 1/30; A61N 1/325; A61N 1/044; A61N 5/0616; A61N 2005/0644;
(Continued)

(56) References Cited

U.S. PATENT DOCUMENTS 5,991,655 A * 11/1999 Gross ..................... A61N 1/044
604/20
2007/0198004 A1    8/2007 Altshuler et al.
(Continued)

FOREIGN PATENT DOCUMENTS

CN    103566466 A    2/2014
CN    204182020 U    3/2015
(Continued)

OTHER PUBLICATIONS

International Search Report cited in PCT/KR2017/005973 dated Oct. 31, 2017, 3 pages.

*Primary Examiner* — Theodore J Stigell
*Assistant Examiner* — Rachel T. Smith
(74) *Attorney, Agent, or Firm* — Rothwell, Figg, Ernst & Manbeck, P.C.

(57) ABSTRACT

Provided is an iontophoresis device. An iontophoresis device according to an embodiment of the present invention includes a power supply unit configured to supply power; two electrodes configured to supply current to a user's skin when brought into contact with the skin, thereby allowing an ionic drug or an active ingredient applied to the user's skin to permeate the skin by an electrical repulsive force; and a control unit configured to adjust an output value of a voltage (Continued)

or a current applied to the electrodes according to the user's skin condition, thereby allowing the user to feel a uniform intensity of electrical stimulation.

13 Claims, 18 Drawing Sheets

(51) Int. Cl.
  *A61N 1/04* (2006.01)
  *A61N 5/06* (2006.01)
  *A61N 1/08* (2006.01)
(52) U.S. Cl.
  CPC ...... *A61N 1/0428* (2013.01); *A61N 2001/083* (2013.01); *A61N 2005/0632* (2013.01); *A61N 2005/0644* (2013.01); *A61N 2005/0652* (2013.01); *A61N 2005/0663* (2013.01)
(58) Field of Classification Search
  CPC ............ A61N 1/0428; A61N 2001/083; A61N 2005/0632; A61N 2005/0652; A61N 2005/0663
  See application file for complete search history.

(56) References Cited

U.S. PATENT DOCUMENTS

| 2008/0119913 | A1* | 5/2008 | Powell ................. A61N 5/0616 607/88 |
| 2016/0310727 | A1* | 10/2016 | Planard-Luong .... A61N 1/0428 |
| 2016/0310728 | A1* | 10/2016 | Cazares Delgadillo ..................... A45D 34/041 |

FOREIGN PATENT DOCUMENTS

| JP | 2005000276 A | 1/2005 |
| JP | 2009532079 A | 9/2009 |
| JP | 2013154229 A | 8/2013 |
| JP | 2014124476 A | 7/2014 |
| KR | 10-400870 B1 | 10/2003 |
| KR | 10-2004-0108505 A | 12/2004 |
| KR | 10-0773119 B1 | 11/2007 |
| KR | 10-2009-0056985 A | 6/2009 |
| KR | 20-2010-0000861 U | 1/2010 |
| KR | 20100021290 A | 2/2010 |
| KR | 20110018021 A | 2/2011 |
| KR | 20110083169 A | 7/2011 |
| KR | 10-2014-0137860 A | 12/2014 |
| KR | 101544046 B1 | 8/2015 |
| KR | 10-1576646 B | 12/2015 |

* cited by examiner

IONTOPHORESIS DEVICE, IONTOPHORESIS METHOD, AND SKIN CARE DEVICE INCLUDING SAME

CROSS REFERENCE TO RELATED APPLICATION

This application is a 35 U.S.C. 371 National Phase Entry Applications from PCT/KR2017/005973, filed Jun. 8, 2017, which claims the benefit of Korean Patent Application Nos. 10-2016-0071174, 10-2016-0071184 and 10-2016-0071194 filed on Jun. 8, 2016, the disclosures of which are incorporated herein in their entirety by reference.

TECHNICAL FIELD

The present invention relates to an iontophoresis device, an iontophoresis method, and a skin care device including the iontophoresis device.

BACKGROUND ART

Iontophoresis is a method of allowing a charged drug or an active ingredient to permeate the skin by an electrical repulsive force by supplying micro-current to the skin, thereby increasing the absorption of such substances into the skin.

That is, iontophoresis is a medication method which is capable of actively increasing drug penetration by forcibly changing an electrical environment of the skin much more than the existing methods but is much less invasive than an injection method.

Currently, iontophoresis devices have been produced which induce an electric field around the skin by applying a cosmetic ingredient having antioxidant and skin protecting functions to the skin and then supplying micro-current to an electrode in contact with the skin.

However, the existing iontophoresis devices are simply configured such that an intensity of stimulation is set to strong, middle, or weak and are operated to apply a certain intensity of electric stimulation to allow cosmetic ingredients to permeate a user's skin.

Accordingly, the same intensity of electric stimulation is applied during every use and thus an intensity of stimulation that the user may feel varies according to the user's skin condition.

Small-sized skin care devices directly or indirectly emitting laser beams of a certain wavelength band to a human skin to regenerate and activate the skin have been developed.

However, the existing skin care devices are disadvantageous in that the number of components is large and thus assembly productivity is low.

Furthermore, the existing skin care devices use a light source that generates the same wavelength when a light source that generates a certain wavelength is provided for skin improvement effects. Thus, effects which may be obtained through one device are limited.

In other words, a light source generating a wide range of wavelengths according to the type of skin disease or trouble is needed but only one wavelength can be generated by the existing skin care devices, thereby decreasing the effect and efficiency thereof.

To solve such problems, a skin care device including a plurality of light sources generating different wavelengths has been proposed. However, the light sources applied thereto are achieved by mounting a plurality of light sources having different wavelength bands, and therefore the number of light sources to be mounted thereon inevitably increases. When the number of light sources having different wavelength bands is increased, the number of light sources to be mounted on a substrate increases in proportion thereto.

DISCLOSURE

Technical Problem

To address the above-described problems, the present invention is directed to providing an iontophoresis device and an iontophoresis method in which a user may always feel a uniform intensity of electric stimulation by appropriately adjusting an output value according to a user's skin conditions, and a skin care device including the iontophoresis device.

The present invention is also directed to providing a skin care device which is capable of preventing foreign materials from sticking thereto and improving assembly productivity by manufacturing some of the components integrally through insert injection molding.

The present invention is also directed to providing a light source for a skin care device, which is capable of obtaining various skin improving effects through a single device by emitting light of different wavelength bands though a single light source, and a skin care device including the same.

Technical Solution

One aspect of the present invention provides an iontophoresis device including a power supply unit configured to supply power, two electrodes configured to supply current to a user's skin when brought into contact with the skin, thereby allowing an ionic drug or an active ingredient applied to the user's skin to permeate the skin by an electrical repulsive force; and a control unit configured to adjust an output value of a voltage or a current applied to the electrodes according to the user's skin condition, thereby allowing the user to feel a uniform intensity of electrical stimulation.

Another aspect of the present invention provides a skin care device including the iontophoresis device and at least one light source configured to generate light having a certain wavelength band and emit the light toward a user's skin.

Another aspect of the present invention provides an iontophoresis method of supplying current to a user's skin to allow an ionic drug or an active ingredient applied to the user's skin to permeate the skin by an electrical repulsive force when contacting with the skin, wherein an output value of a voltage or a current applied to the at least one electrode which is in contact with the skin is adjusted according to the user's skin condition to allow the user to feel a uniform intensity of electrical stimulation.

Another aspect of the present invention provides a skin care device including a case part including a body having an inner space, a pair of contact electrodes disposed at one side of the body and configured to change an electrical environment of a user's skin by generating a potential difference on the user's skin when power is supplied thereto, and a translucent member, a frame part inserted and disposed in the inner space and configured to fix a circuit board on which at least one light source is mounted; and a cap part to which the frame part is detachably coupled and which is coupled to the case part to close an open bottom portion of the inner space.

Another aspect of the present invention provides a light source, for a skin care device, which includes a mold body including a receiving portion formed at a predetermined depth on a top surface thereof, a plurality of first electrodes and a plurality of second electrodes each of which has one end exposed via a bottom surface of the receiving portion and to which power having different polarities are supplied, a plurality of light-emitting diodes (LEDs), each of which is individually mounted on one of the first electrode and second electrode and connected to other electrode via a wire; and an encapsulant configured to be filled in the receiving portion, wherein the plurality of LEDs have different wavelength bands each other; and a skin care device including the light source.

Advantageous Effects

According to the present invention, an output value may be appropriately adjusted according to a user's skin condition so that the user may always feel a uniform intensity of electrical stimulation, thereby preventing pain due to the electrical stimulation.

According to the present invention, some of the components of a skin care device may be integrally formed by insert injection molding to prevent foreign substances from sticking thereto and increase assembly productivity.

Furthermore, according to the present invention, light having different wavelength bands may be emitted from one light source, thereby simultaneously achieving various skin improving effects with one device.

DESCRIPTION OF DRAWINGS

FIGS. 3A to 3C are diagrams illustrating current waveforms of an output value when pulse current is supplied to an iontophoresis device according to an embodiment of the present invention, in which FIG. 3A illustrates a case in which a duty ratio of the pulse current is 30%, FIG. 3B illustrates a case in which the duty ratio of the pulse current is 50%, and FIG. 3C illustrates a case in which the duty ratio of the pulse current is 70%.

MODES OF THE INVENTION

Figure 1:
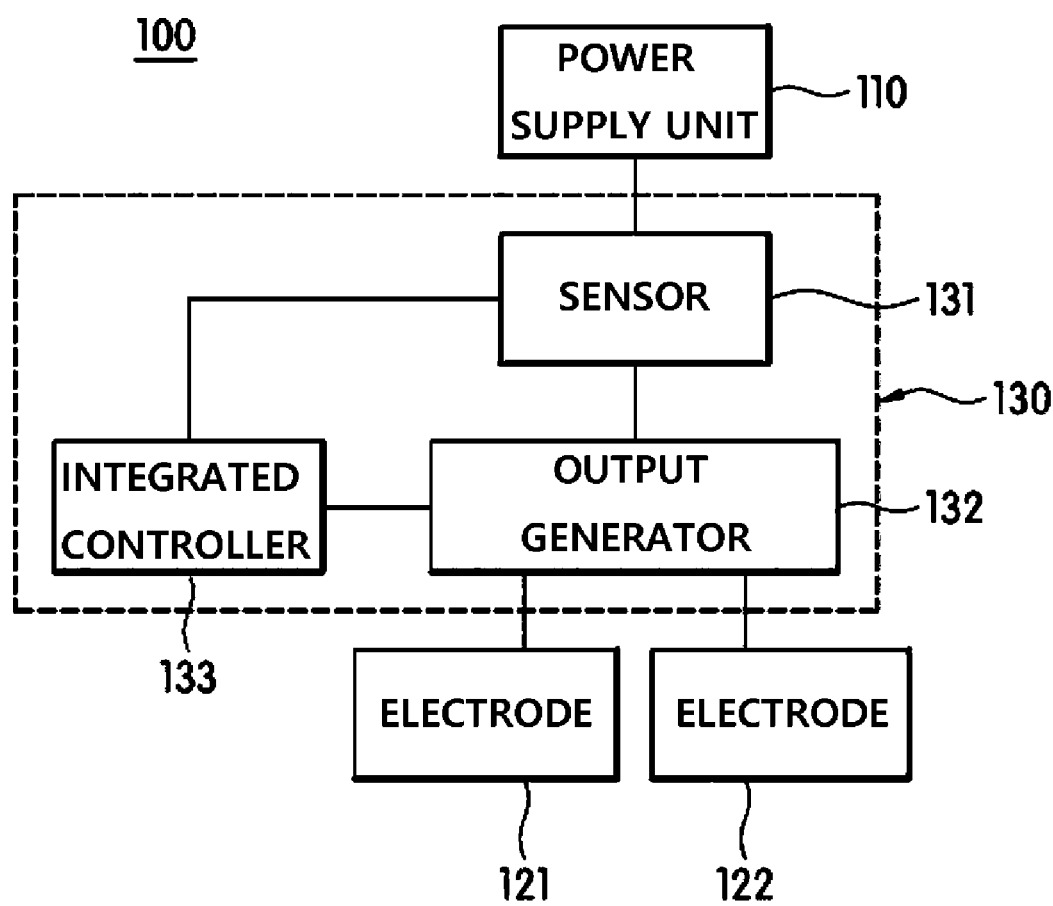
FIG. 1 is a block diagram of an iontophoresis device according to an embodiment of the present invention.
Figure 2:
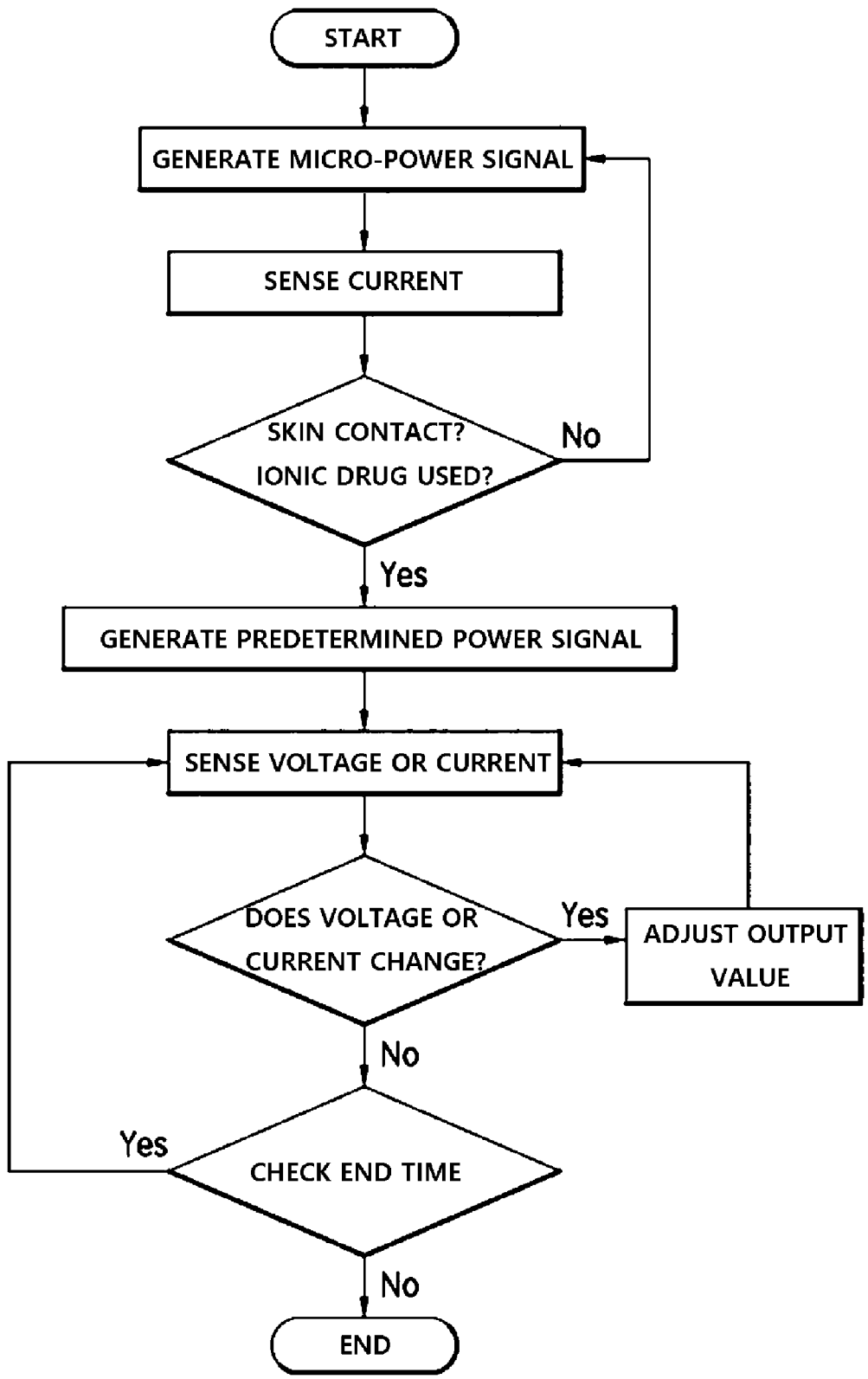
FIG. 2 is a flowchart of an algorithm of an iontophoresis device according to an embodiment of the present invention.

Hereinafter, embodiments of the present invention will be described in detail with reference to the accompanying drawings so that those of ordinary skill in the art can easily implement them. The present invention may be embodied in many different forms and is not limited to embodiments set forth herein. In the drawings, parts that are not related to a description of the present invention are omitted for clarity, and the same reference numerals are assigned to the same or like components throughout the disclosure.

As shown in FIG. 1, an iontophoresis device 100 according to an embodiment of the present invention includes a power supply unit 110, two contact electrodes 121 and 122, and a control unit 130.

The two contact electrodes 121 and 122 are configured to, when power is supplied thereto, increase the permeation of an ionic drug or an active ingredient into a user's skin by changing an electrical environment of the skin by generating a potential difference on the user's skin.

That is, the two contact electrodes 121 and 122 are configured to implement an iontophoresis function. When current is supplied to the user's skin using power supplied from the power supply unit 110, the user's skin and the two contact electrodes 121 and 122 may form a closed circuit and thus ion movement may occur. Here, the power supply unit 110 may be a well-known battery. When the iontophoresis device 100 according to the present invention is applied to a skin care device 1000, the power supply unit 110 may be a battery (see reference number 110 of FIG. 5) for driving the skin care device 1000.

For example, when the ionic drug or the active ingredient is applied to the user's skin, the two contact electrodes 121 and 122 are brought into contact with the user's skin, and then current is supplied to the two contact electrodes 121 and 122, the ionic drug or the active ingredient applied to the user's skin is ionized and thus may easily permeate the tissues in the skin via the mucous membrane of the skin, thereby achieving an ion introduction effect.

In this case, when the current flows through the user's skin via the two contact electrodes 121 and 122 using the power supplied from the power supply unit 110, the amount of the current flowing through the user's skin may vary according to the user's skin condition. Thus, even if the same voltage is applied to the two contact electrodes 121 and 122, an intensity of electrical stimulation that the user feels may also vary according to the user's skin condition.

This is because a skin resistance may vary according to a moisture content of the user's skin, the thickness of the user's skin, or a thickness of the ionic drug or the active ingredient applied to the user's skin to achieve the iontophoresis function.

For example, even if the same voltage is applied to the contact electrodes 121 and 122, a skin resistance when the user's skin is dry with a low moisture content or is thick may be greater than that when the user's skin is moist with a high moisture content or is thin. Accordingly, when the user's skin is dry with the low moisture content or is thick, the amount of current flowing though the user's skin decreases and thus the intensity of electric stimulation that the user feels may be weak. In contrast, when the user's skin is moist with a high water content or is thin, the skin resistance is less than that in the aforementioned case and thus the amount of current flowing through the user's skin increases and the intensity of electrical stimulation that the user feels may be relatively strong.

Furthermore, even if the same voltage is applied to the contact electrodes 121 and 122, the amount of current flowing through the ionic drug or the active ingredient when the thickness of the ionic drug or the active ingredient applied to the user's skin is thin may be less than that when the thickness of the applied ionic drug or active ingredient is thick. Thus, the intensity of electrical stimulation that the user feels may be lower than that when the thickness of the applied ionic drug or active ingredient is thick. In contrast, when the thickness of the ionic drug or the active ingredient applied to the user's skin is thick, the amount of current flowing through the ionic drug or the active ingredient relatively increases than that in the aforementioned case and thus the intensity of electrical stimulation that the user feels may be relatively strong.

In the present invention, an output value of a voltage or a current applied to the contact electrodes 121 and 122 is adjusted according to the user's skin condition such that the intensity of electrical stimulation that the user feels may be always the same regardless of the user's skin condition.

Here, factors that determine the user's skin condition include at least one among a moisture content of the surface of the user's skin, the thickness of the user's skin in contact with the contact electrodes 121 and 122, whether an ionic drug or an active ingredient is applied or not, and an applied thickness of the ionic drug or the active ingredient.

For example, the output value may be adjusted by changing a voltage, a current, or a duty ratio b/a of a pulse current applied to the contact electrodes 121 and 122. The voltage, the current, or the duty ratio b/a of the pulse current applied to the contact electrodes 121 and 122 may be changed on the basis of the amount of change in the voltage or the current according to a condition of the user's skin which is in contact with the two contact electrodes 121 and 122 when power is supplied.

To this end, the control unit 130 may include a sensing part 131 measuring a user's skin condition, an integrated control part 133 identifying the user's skin condition measured by the sensing part 131 and controlling overall operations, and an output generating part 132 changing an output value according to a signal output from the integrated control part 133.

Here, the control unit 130 may be a chipset mounted on one surface of a circuit board 244 and may control overall operations of the skin care device 1000 when the iontophoresis device 100 according to the present invention is applied to the skin care device 1000. Furthermore, the integrated control part 133 may calculate an output value output from the output generating part 132 on the basis of the amount of change in a voltage or a current varying according to the user's skin condition.

In this case, the sensing part 131 may determine whether the two contact electrodes 121 and 122 and the user's skin are in contact with each other on the basis of the voltage or the current measured between the two contact electrodes 121 and 122.

For example, since a resistance is infinite during the supply of power when the two contact electrodes 121 and 122 are not in contact with the user's skin, current does not flow therethrough and a voltage between the two contact electrodes 121 and 122 may be equal to a voltage applied thereto.

In contrast, current flows through the user's skin during the supply of power when the two contact electrodes 121 and 122 are in contact with the user's skin, and thus a certain current may be measured or a voltage drop may occur due to a skin resistance.

Based on the above principle, the control unit 130 may determine that the two contact electrodes 121 and 122 are in contact with the user's skin when the amount of change in the voltage or the current measured by the sensing part 131 is greater than or equal to a predetermined level during the supply of power and apply a certain output value to the two contact electrodes 121 and 122 via the output generating part 132.

Here, the amount of change in the voltage or the current according to the user's skin condition may be stored in a lookup table and thus the integrated control part 133 may change a voltage, a current, or a duty ratio of a pulse current output via the output generating part 132. The amount of change in the voltage or the current stored in the lookup table may be information matching the amount of change in the voltage or the current measured by the sensing part 131 in a one to one manner.

For example, when the amount of change in a voltage between the two contact electrodes 121 and 122 is 1 V or more, the control unit 130 may determine that the contact electrodes 121 and 122 are in contact with the user's skin and apply a certain voltage (e.g., 25 V) to the contact electrodes 121 and 122.

In this state, when the amount of change in the voltage applied to the two contact electrodes 121 and 122 according to the user's skin condition is 1 V or more, the control unit 130 may identify the user's skin condition using the integrated control part 133 on the basis of the amount of change in the voltage measured by the sensing part 131, and a voltage may be appropriately output within a range of 20 to 25 V from the output generating part 132 according to the identified user's skin condition or the amount of current to be supplied to the user's skin may be adjusted through variable resistance. This allows the user to feel a uniform intensity of electrical stimulation regardless of the user's skin condition.

That is, the integrated control part 133 may reduce an output voltage to be output from the output generating part 132 to up to 20 V to reduce the intensity of stimulation when the user's skin is moist and thus current may smoothly flow through the user's skin and may increase an output voltage to be output from the output generating part 132 to up to 25 V to increase the intensity of stimulation when the user's skin is dry and thus the amount of current flowing through the user's skin is relatively small, thereby allowing the user to feel a uniform intensity of stimulation during every use regardless of the user's skin condition.

Alternatively, when the amount of change in a voltage between the two contact electrodes 121 and 122 is 1 V or more, the control unit 130 may identify that the contact electrodes 121 and 122 are in contact with the user's skin and supply a pulse current having a duty ratio of 30% to the contact electrodes 121 and 122.

In this state, when a voltage between the two contact electrodes 121 and 122 changes according to the user's skin condition, the control unit 130 may identify the user's skin condition using the integrated control part 133 on the basis of the amount of change in the voltage measured by the sensing part 131 and may control the output generating part 132 to output a pulse current in a duty ratio of 25 to 35% according to the identified user's skin condition, thereby allowing the user to feel a uniform intensity of electrical stimulation.

That is, the integrated control part 133 may reduce a duty ratio of a pulse current to be output from the output generating part 132 to up to 25% to reduce the intensity of stimulation when the user's skin is moist and thus current may smoothly flow through the user's skin and increase the duty ratio of the pulse current to be output from the output generating part 132 to up to 35% to increase the intensity of stimulation when the user's skin is dry and thus the amount of current flowing through the user's skin is relatively small. Accordingly, the user may always feel a uniform intensity of stimulation regardless of the user's skin condition as described above.

Furthermore, in the iontophoresis device 100 according to the present invention, the amount of change in a voltage may be measured in real time by the sensing part 131 and thus the integrated control part 133 may control the output generating part 132 to output an output value appropriate for a current condition of the user's skin even when an ionic drug or an active ingredient applied to the user's skin permeates the user's skin and thus the user's skin condition is changed. Thus, the user may always feel a uniform intensity of electrical stimulation during every operation of the iontophoresis device 100.

It has been described above that, in the present invention, a voltage applied to adjust the intensity of electrical stimulation that a user feels changes within a range of 20 to 25 V or a duty ratio of a pulse current applied to adjust the intensity of electrical stimulation changes within a range of 25 to 35%, but the present invention is not limited thereto and the ranges may be variously changed according to design conditions.

When the iontophoresis device 100 according to the present invention is driven through manipulation of a switch unit 140 (see FIG. 5), the same voltage may be always applied to the contact electrodes 121 and 122, but a voltage applied to the contact electrodes 121 and 122 to determine whether the two contact electrodes 121 and 122 are in contact with the user's skin may be lower than that applied to the two contact electrodes 121 and 122 to allow an ionic drug or an active ingredient applied to the user's skin to permeate the user's skin.

That is, a low voltage, e.g., about 10 V, may be applied to determine whether the contact electrodes 121 and 122 are in contact with the user's skin at an initial stage at which the iontophoresis device 100 is driven through the manipulation of the switch unit 140, and a voltage, e.g., 25 V, higher than that at the initial stage may be applied to the two contact electrodes 121 and 122 when it is determined that the contact electrodes 121 and 122 are in contact with the user's skin so that the ionic drug or active ingredient applied to the user's skin may smoothly permeate the user's skin. This is to prevent unnecessary power consumption in a standby state so that a duration of use of the power supply unit 110 may be increased.

Alternatively, the iontophoresis device 100 according to the present invention may be changed to a plurality of output modes having output values of different ranges through control of the control unit 130 during the user's manipulation of the switch unit 140. For example, the switch unit 140 may be embodied as at least one button 142 capable of being pressed by the user. An intensity of electric stimulation may be switched between different modes, e.g., a strong mode, a normal mode, and a weak mode, according to a control signal from the control unit 130 on the basis of a number of times the button 142 is pressed.

In detail, a voltage applied to the two contact electrodes 121 and 122 may be changed to be within a range of 35 to 45 V according to the user's skin condition when the control unit 130 is driven in the strong mode through the user's manipulation of the button 142, may be changed to be within a range of 25 to 35 V according to the user's skin condition when the control unit 130 is driven in the normal mode through the user's manipulation of the button 142, and may be changed to be within a range of 15 to 25 V according to the user's skin condition when the control unit 130 is driven in the weak mode through the user's manipulation of the button 142.

Figure 3A:
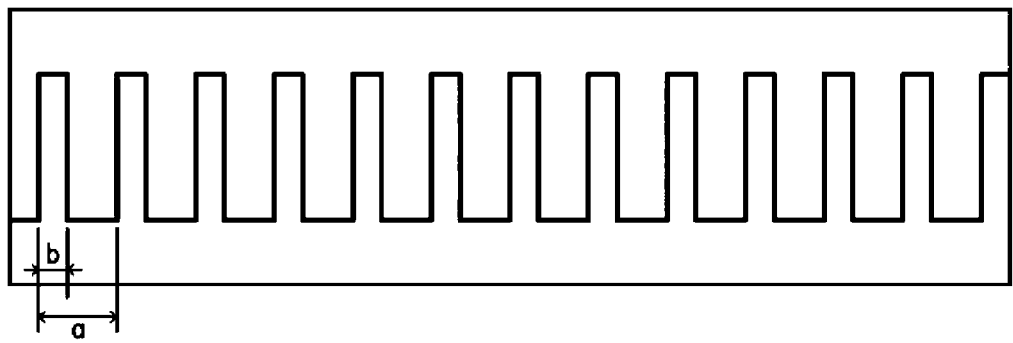
Figure 3B:
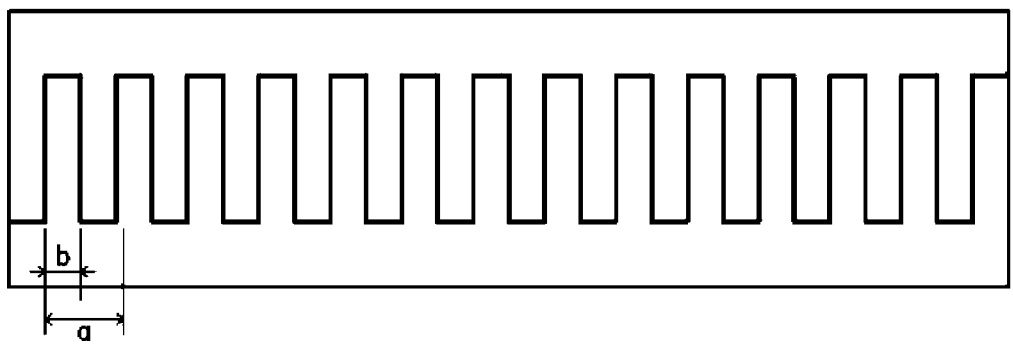
Figure 3C:
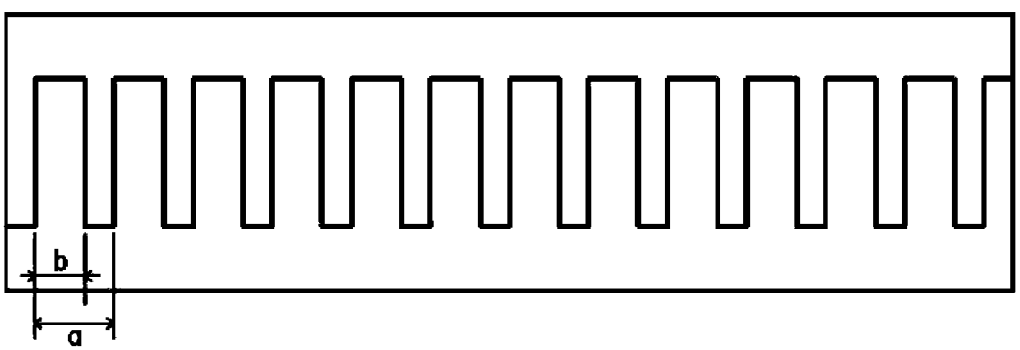

As another example, a duty ratio of a pulse current applied to the two contact electrodes 121 and 122 may be changed to be within a range of 60 to 80% according to the user's skin condition when the control unit 130 is driven in the strong mode through the user's manipulation of the button 142, may be changed to be within a range of 40 to 60% according to the user's skin condition when the control unit 130 is driven in the normal mode through the user's manipulation of the button 142, and may be changed to be within a range of 20 to 40% according to the user's skin condition when the control unit 130 is driven in the weak mode through the user's manipulation of the button 142 (see FIGS. 3A to 3C).

Accordingly, the user may select an intensity of electrical stimulation to be applied to the user's skin by selecting one of the strong mode, the normal mode, and the weak mode as an output mode for driving the control unit 130 through manipulation of the button 142, and an output value for the selected output mode may be adjusted within a predetermined range according to the user's skin condition so that the user may feel a desired intensity of electrical stimulation regardless of the user's skin condition.

For example, when the iontophoresis device 100 according to the present invention is operated in the strong mode, the user may adjust a voltage to be applied to the contact electrodes 121 and 122 according to a current condition of the user's skin, and may feel an intensity of electrical stimulation obtained when about 40V is applied in a normal skin condition. Even when the user's skin condition is changed due to the permeation of ionic drug or active ingredient thereinto, a voltage to be applied to the contact electrodes 121 and 122 may be adjusted according to the changed skin condition so that the user may feel an intensity of electrical stimulation obtained when about 40 V is applied under a normal skin condition.

The above-described iontophoresis device 100 according to the present invention is applicable to the skin care device 1000 having at least one light source 300 generating light which has a certain wavelength band and which emits the light toward the user's skin as illustrated in FIGS. 4 to 12.

Thus, not only a skin improving effect using the light source 300 but also an effect of permeation of an ionic drug or an active ingredient into the skin through the iontophoresis device 100 may be achieved.

Figure 4:
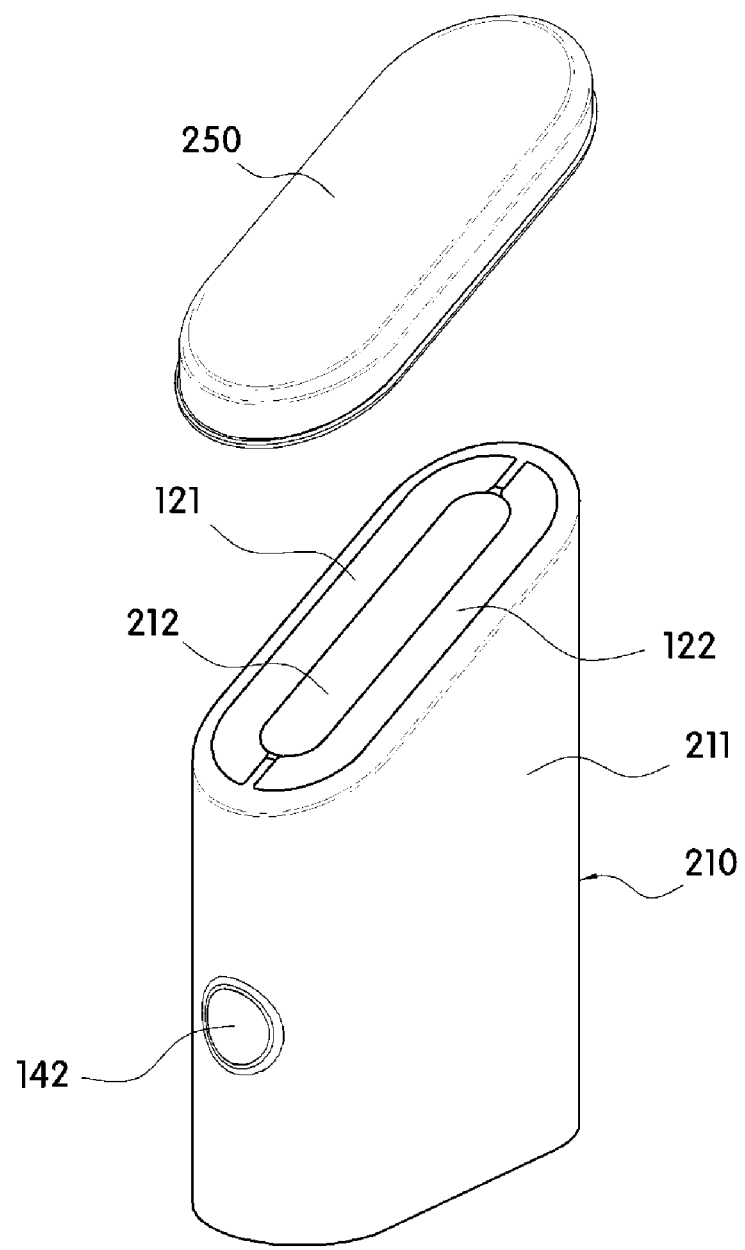
FIG. 4 is a schematic view of a skin care device to which an iontophoresis device according to an embodiment of the present invention is applied.
Figure 5:
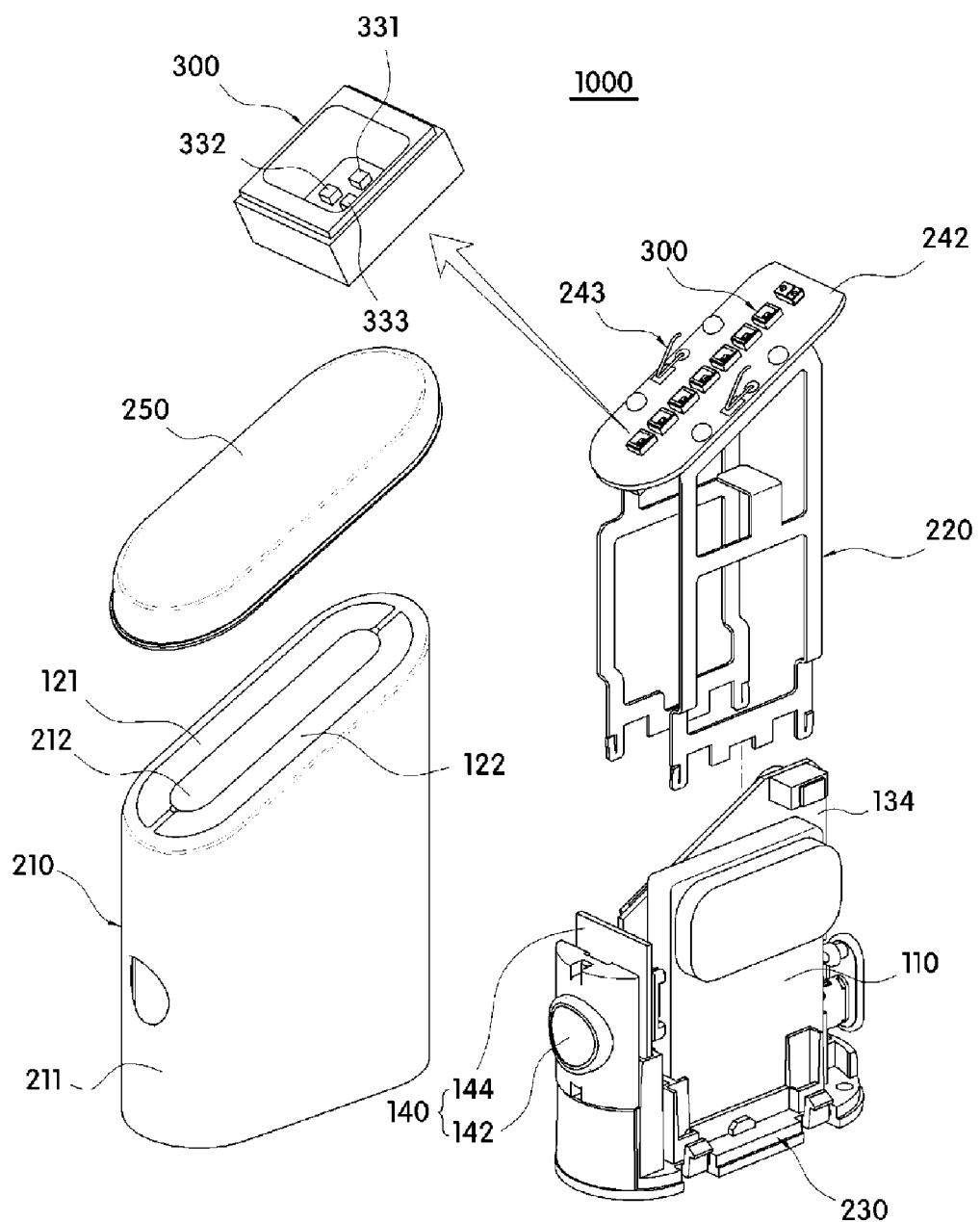
FIG. 5 is an exploded view of main components of FIG. 4.
Figure 6:
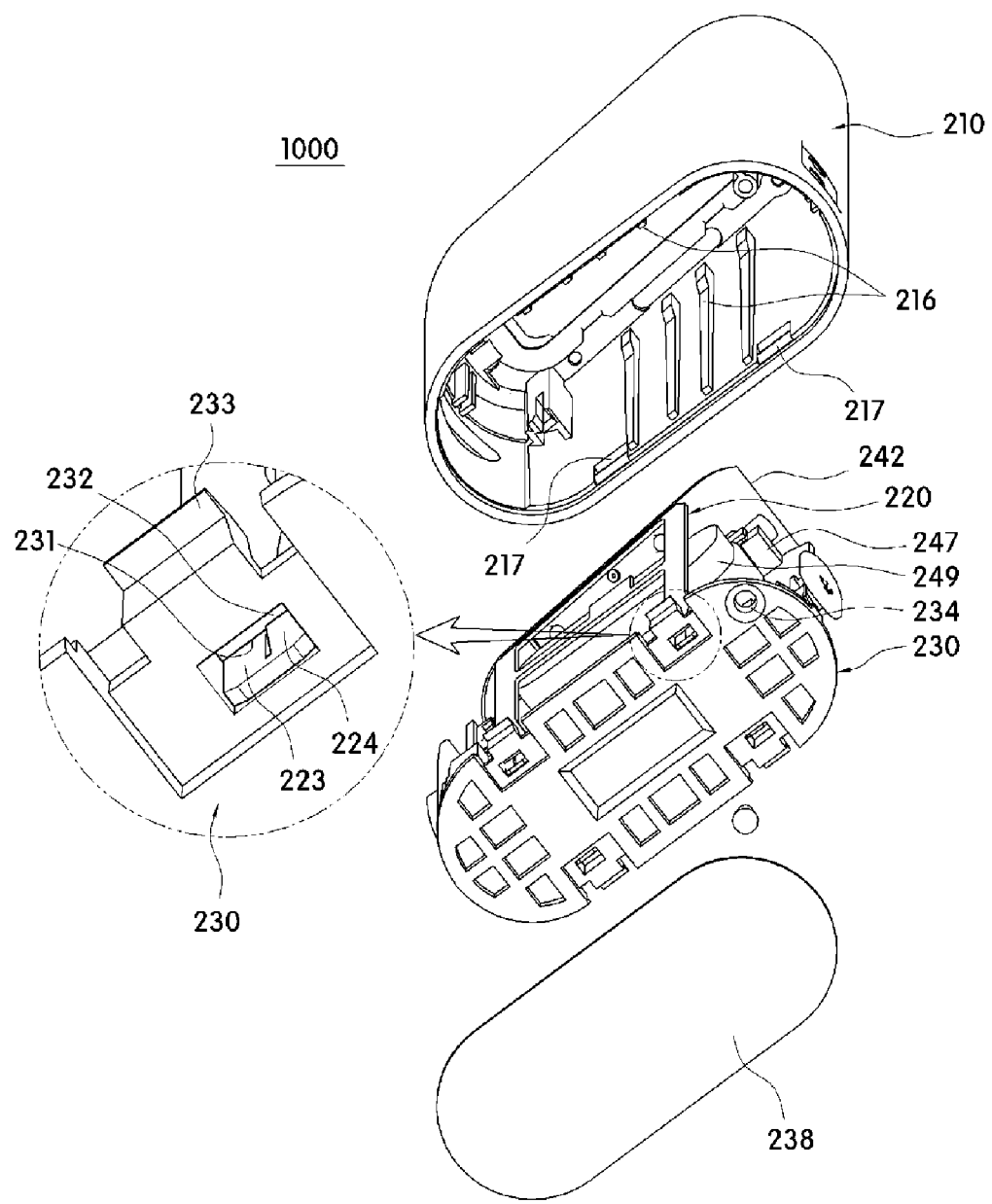
FIG. 6 is a bottom view of FIG. 5.
Figure 7:
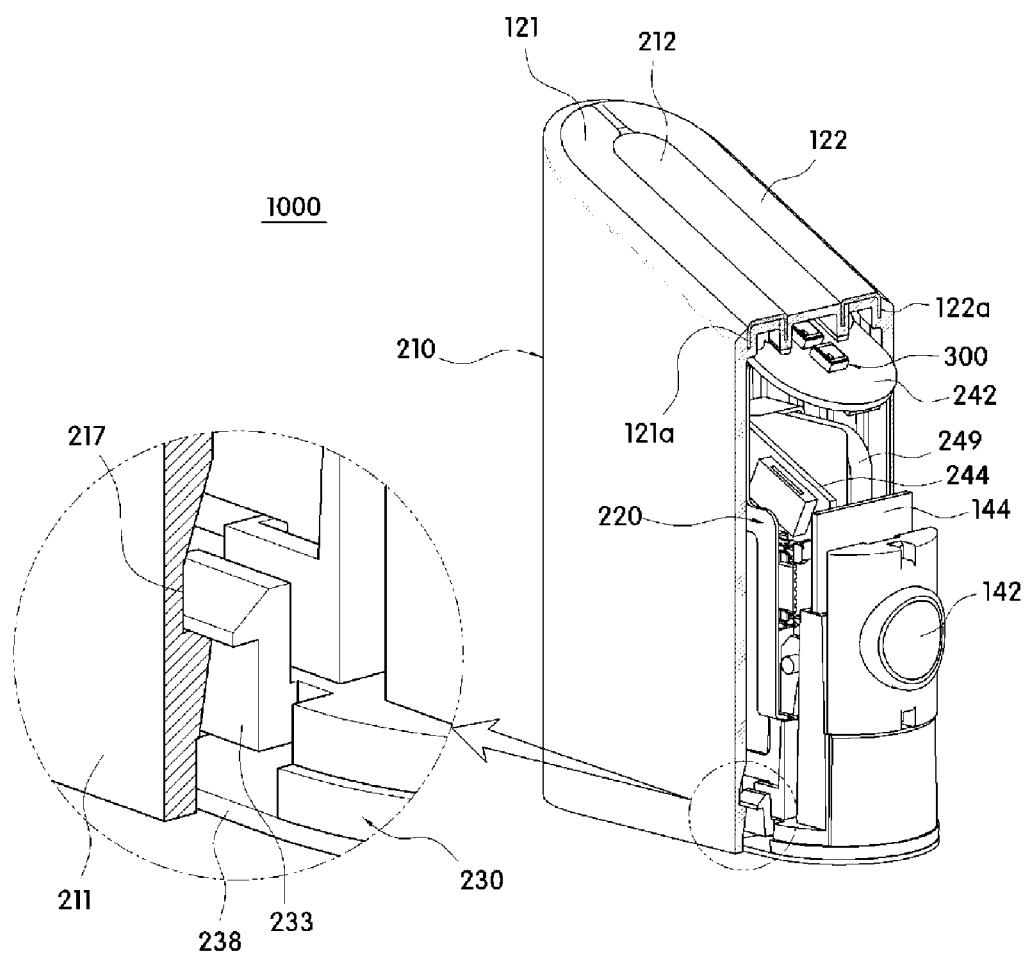
FIG. 7 is a partial cutaway view illustrating a coupling relation between a cap part and a case part.
Figure 8:
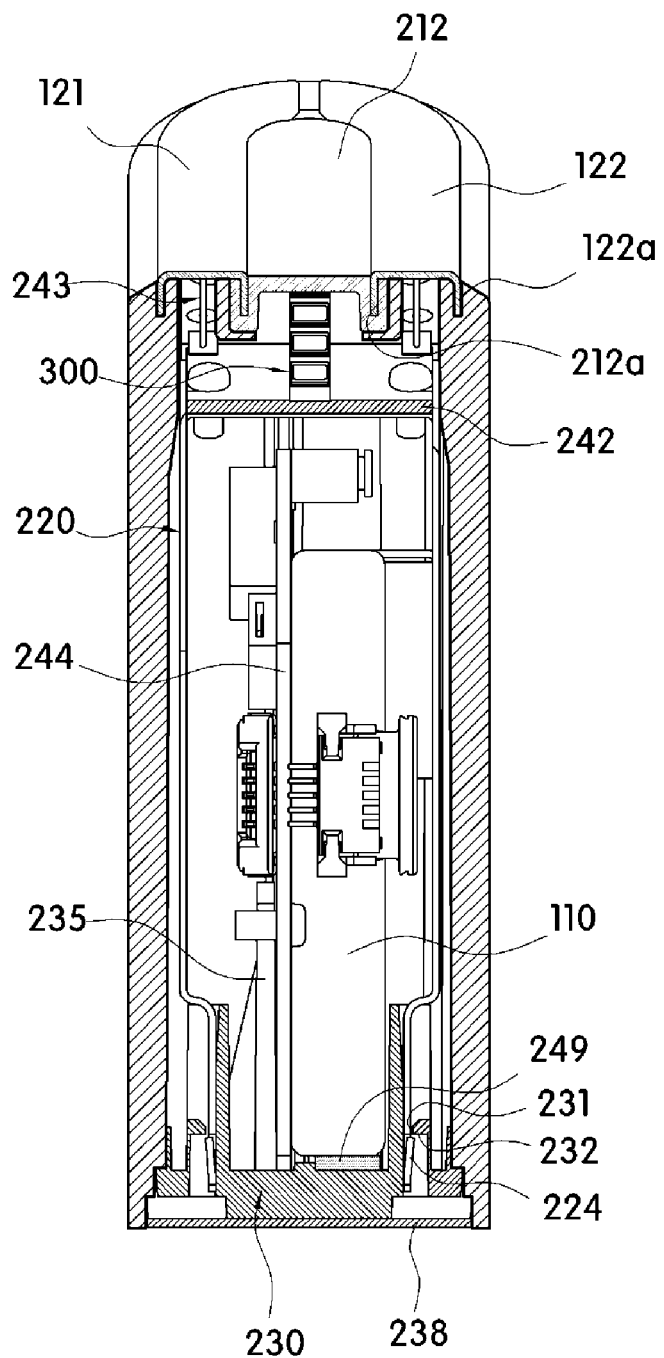
FIG. 8 is a diagram illustrating an internal coupling state of a skin care device according to an embodiment of the present invention.
Figure 9:
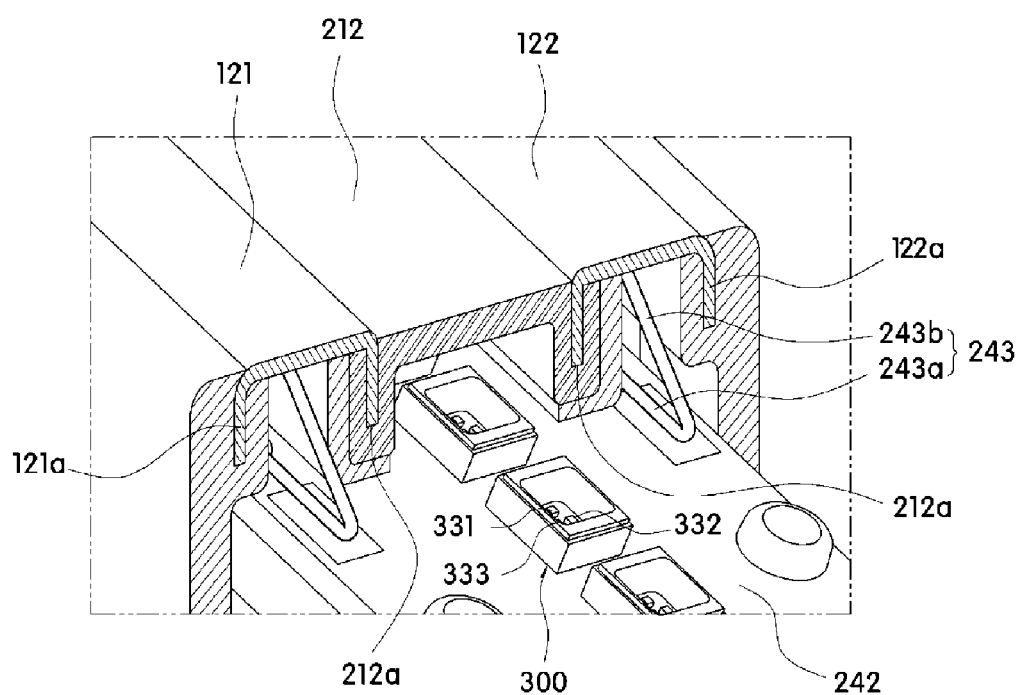
FIG. 9 is a partially cutaway enlarged view illustrating an arrangement relationship among contact electrodes, a translucent member, and an elastic member of a skin care device according to an embodiment of the present invention.
Figure 10:
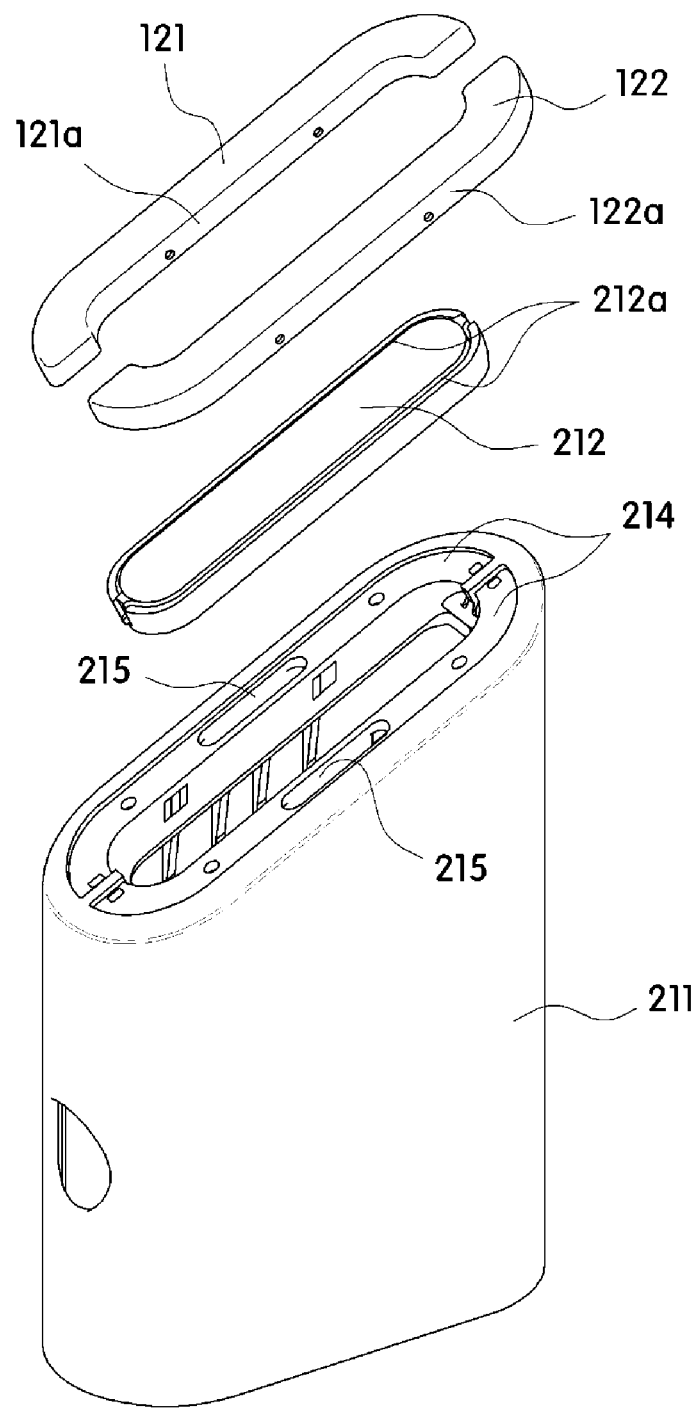
FIG. 10 is a diagram illustrating a state in which a translucent member, contact electrodes, and a body are forcibly separated from a skin care device according to an embodiment of the present invention.
Figure 11:
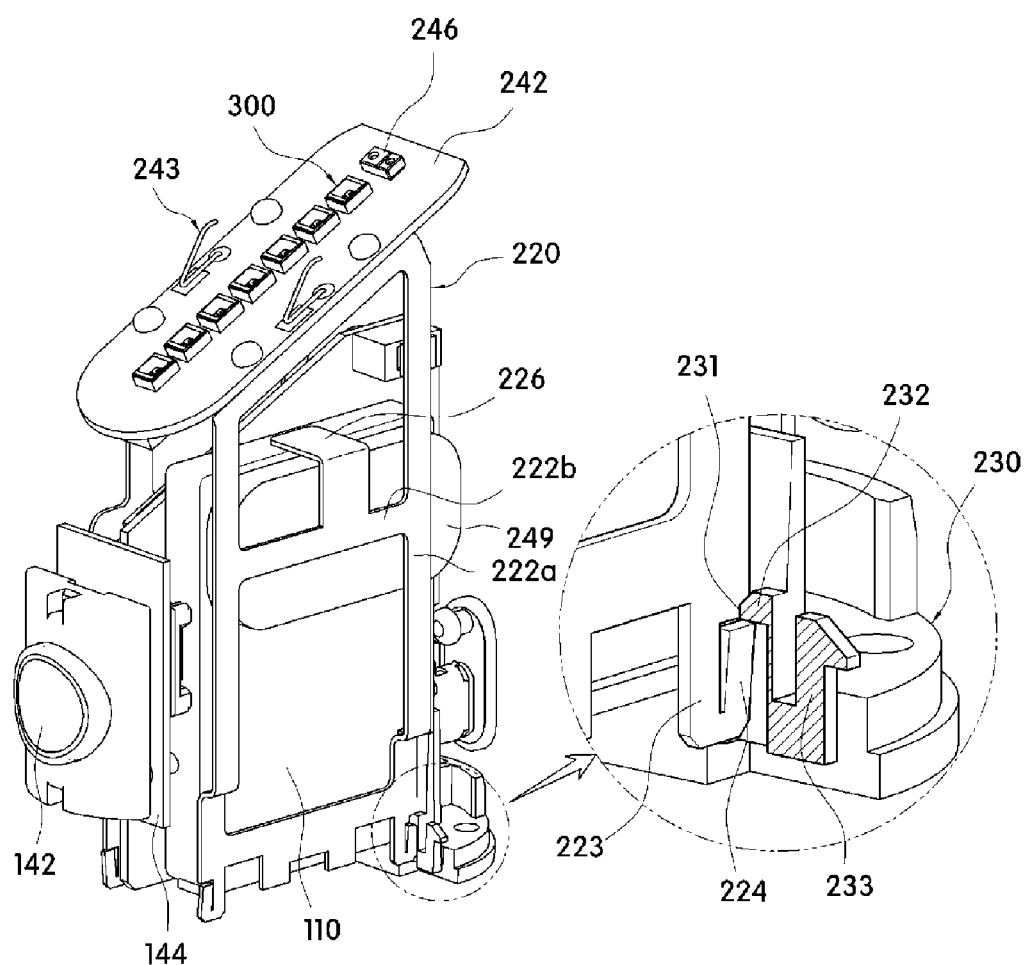
FIG. 11 is a diagram illustrating a coupling relation between a cap part and a frame part of a skin care device according to an embodiment of the present invention.
Figure 12:
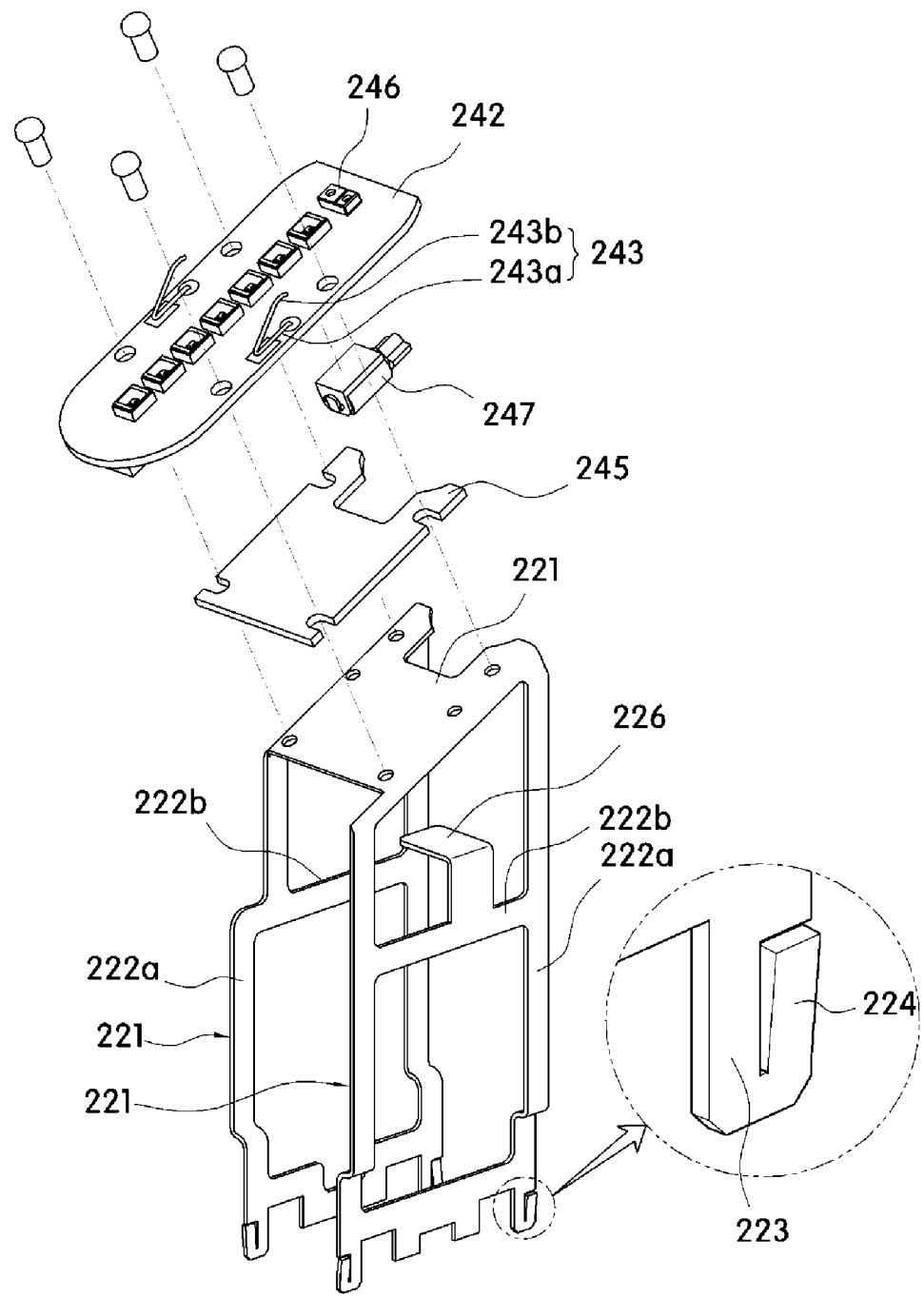
FIG. 12 is a diagram illustrating a state in which a circuit board having a light source mounted thereon is separated from a frame part in a skin care device according to an embodiment of the present invention.
Figure 13:
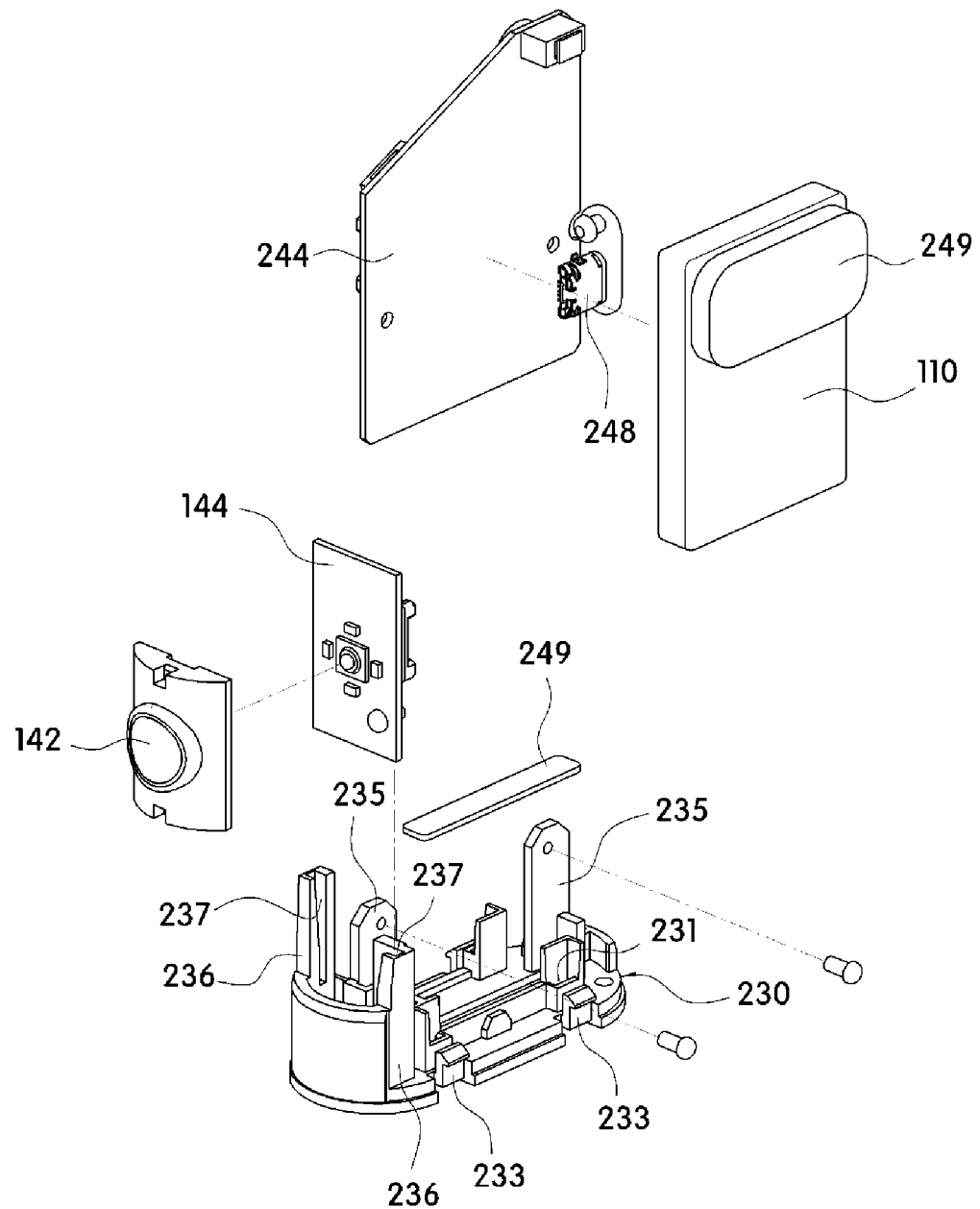
FIG. 13 is a diagram illustrating a state in which a cap part, a button part, a main circuit board, and a battery are separated from a skin care device according to an embodiment of the present invention.
Figure 14:
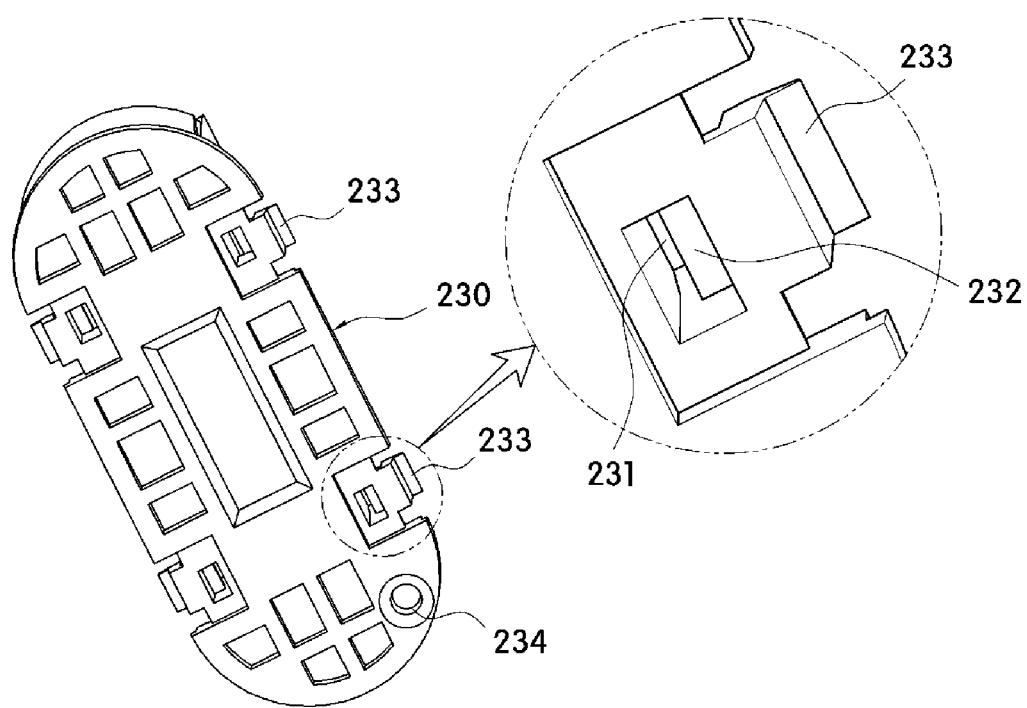
FIG. 14 is a bottom view of a cap part applied to a skin care device according to an embodiment of the present invention.

For example, the skin care device 1000 to which the iontophoresis device 100 according to the present invention is applied may include a case part 210, a frame part 220, and a cap part 230 as illustrated in FIGS. 4 to 6.

The case part 210 forms an external appearance of the skin care device 1000 and may include a body 211 which accommodates various components therein, such as a light source 300, a circuit board 242, and the well-known battery 110 serving as a power supply unit, and which protects the components from an external environment.

That is, the case part 210 may include the body 211 having a box shape with a certain inner space to accommodate the various components therein, and the cap part 230 may be detachably coupled to the body 211.

For example, the bottom of the body 211 may be open such that the various components may be inserted into the inner space and may be closed by the cap part 230 detachably coupled to the bottom of the body 211.

In this case, the two contact electrodes 121 and 122 configured to implement the iontophoresis function may be provided at one side of the body 211 to be exposed to the outside, and a translucent member 212 protecting the light source 300 from an external environment and protecting a user's eyes may be disposed in front of the light source 300.

To this end, a seating plane 214 on which the two contact electrodes 121 and 122 are placed may be provided on a surface of the body 211 and may have a hollow shape extending a certain length inward from an upper edge of the body 211. Furthermore, the translucent member 212 may be located in a hollow portion of the seating plane 214.

In this case, the body 211, the two contact electrodes 121 and 122, and the translucent member 212 may be detachably coupled with one another but may be integrally formed with one another to increase assembly convenience and minimize foreign substances being caught between these components due to the contact with a user's skin during use in the case part 210.

The body 211, the two contact electrodes 121 and 122 and the translucent member 212 may be integrally formed, for example, by insert molding.

That is, the two contact electrodes 121 and 122 and the translucent member 212 may be integrally formed by primary insert molding such that the two contact electrodes 121 and 122 are disposed at an edge of the translucent member 212 while being physically separated from each other.

In this case, a pair of insertion grooves 212a may be formed in the translucent member 212 by cutting an upper surface of the translucent member 212 to a certain depth in a downward direction, and extension parts 121a and 122a may extend downward from edges of the two contact electrodes 121 and 122. Thus, the two contact electrodes 121 and 122 may be integrated with the translucent member 212 by placing the extension parts 121a and 122a into the insertion groove 212a.

Furthermore, the body 211 may be formed by secondary insert molding in a state in which the translucent member 212 and the two contact electrodes 121 and 122 are integrated with one another so that the translucent member 212, the two contact electrodes 121 and 122, and the body 211 may be integrated with one another in the state in which the two contact electrodes 121 and 122 are disposed on the seating plane 214.

In this case, a well-known thermoplastic resin may be used to manufacture the translucent member 212 and the body 211 which are formed by insert injection molding. Furthermore, although the same thermoplastic resin may be used to form the translucent member 212 and the body 211, a thermoplastic resin having a melting point higher than that of a thermoplastic resin used to form the body 211 may be used to form the translucent member 212. This is to prevent the translucent member 212 integrated with the two contact electrodes 121 and 122 by primary insert molding from melting during the secondary insert molding performed for the integration of the translucent member 212 with the body 211.

For example, the translucent member 212 may be formed of a polymer material having a melting point of about 300° C., and the body 211 may be formed of ABS resin having a melting point of about 1000° C. However, the materials of the translucent member 212 and body 211 are not limited thereto, and all well-known thermoplastic resins having different melting points and capable of being injected are available.

The two contact electrodes 121 and 122 may be plate type members having a certain area to increase a contact area thereof with respect to the skin and may be entirely or partially provided on the seating plane 214.

In addition, the edges of the two contact electrodes 121 and 122 connected to the extension parts 121a and 122a may be curved. Thus, the two contact electrodes 121 and 122 may be brought into contact with the user's skin and thus may prevent the user's skin from being damaged by sharp edges during the rubbing of the two contact electrodes 121 and 122 against the user's skin or may prevent the ionic drug or foreign substances on the skin from being scraped and collected by the edges.

In this case, the seating plane 214 may be an inclined plane with a certain slope inclined at a certain angle with respect to a horizontal plane. For example, as illustrated in FIG. 4, the seating plane 214 may include an inclined surface, the left side of which is lower than a right side thereof with respect to the bottom of the case part 210, and the two contact electrodes 121 and 122 may be disposed on the inclined surface.

Accordingly, the two contact electrodes 121 and 122 disposed on the inclined surface may also have the certain slope with respect to the horizontal plane. As a result, an area of contact between the two contact electrodes 121 and 122 and the user's skin may increase when the two contact electrodes 121 and 122 are brought into contact with the user's skin. In addition, a natural contact between the user's skin and the contact electrodes 121 and 122 may be achieved even when the user does not excessively bend his or her wrist to bring the two contact electrodes 121 and 122 into contact with the skin while grasping the body 211 during use.

In this case, the seating plane 214 may be entirely or partially inclined.

The frame part 220 is provided in the inner space of the body 211 and may fix the circuit board 242 on which the light source 300 is mounted such that the light source 300 may be located in a region corresponding to the translucent member 212 when the cap part 230 and the case part 210 are coupled to each other.

To this end, the frame part 220 may include a top plate frame 221, and the circuit board 242 may be detachably coupled to the top plate frame 221.

Here, the top plate frame 221 may be a frame structure, the inside of which is open, or may be a plate type member.

Thus, the circuit board 242 may be fixed onto the frame part 220 via a fastening member such as a bolt member, and the light source 300 mounted on the circuit board 242 may be located in the region corresponding to the translucent member 212 when the cap part 230 and the case part 210 are fastened to each other while a lower portion of the frame part 220 is fixed on the cap part 230.

Here, an insulating member 245 may be provided between the circuit board 242 and the top plate frame 221 to electrically insulate the circuit board 242 and the top plate frame 221 from each other.

In this case, the frame part 220 may include at least one support frame 222 extending downward from the top plate frame 221, and a lower end of the support frame 222 may be detachably coupled to the cap part 230.

In detail, the support frame 222 may include at least one coupling piece 223 to be fastened with the cap part 230, and a coupling hole 231 may be formed at a location on the cap part 230 corresponding to the coupling piece 223 to pass through the cap part 2230.

In this case, the coupling piece 223 may include a cut piece 224 being partially cut so the coupling piece 223 may be elastically deformed. One end of the cut piece 224 may outwardly protrude from a surface of the coupling piece 223.

Accordingly, when the cut piece 224 and the cap part 230 are coupled to each other, the cut piece 224 may be elastically deformed by an external force, be inserted into the coupling hole 231, and return to its original state to be hooked at an edge of the coupling hole 231, thereby preventing the cut piece 224 from being separated from the coupling hole 231.

Here, the cut piece 224 may be formed at a central portion of the coupling piece 223 but may be formed at one side of the coupling piece 223.

In this case, a hooking groove 232 may be formed to a certain depth in a bottom surface of the cap part 230 to be connected with the coupling hole 231. When the cap part 230 is coupled to the frame part 220, an end portion of the cut piece 224 passing through the coupling hole 231 may be hooked by the hooking groove 232.

Thus, when the cap part 230 and the frame part 220 need to be reassembled or separated from each other, the cut piece 224 exposed via the hooking groove 232 may be pressurized by a tool such as a driver to easily separate the cap part 230 and the frame part 220 from each other.

Accordingly, when the cap part 230 and the frame part 220 need to be reassembled or separated from each other, the cut piece 224 may be elastically deformed by applying an external force thereto to release a latching force by the cut piece 224. Thus, the cap part 230 and the frame part 220 may be separated from each other by allowing the cut piece 224 deformed by the external force to pass through the coupling hole 231.

Here, a pair of support frames 222 extending downward from both ends of the top plate frame 221 may be provided, and a pair of vertical bars 222*a* having a certain length and extending from the side ends of the top plate frame 221 may be provided to be connected to each other via at least one support bar 222*b*.

The support frame 222 may include at least one protruding bar 226 protruding a certain length from the body 211 to the inner space. Thus, when the cap part 230 and the frame part 220 are coupled to each other, upward movement of the battery 110 inside the frame part 220 may be restrained.

For example, the protruding bar 226 may extend a certain distance inward from the support bar 222*b*, and a top surface of the battery 110 may be in contact with a bottom surface of the support bar 222*b*.

When, for the iontophoresis function, the two contact electrodes 121 and 122 are provided on a surface of the case part 210, the two contact electrodes 121 and 122 may be electrically connected to the circuit board 242 having mounted thereon the light source 300 through a contact method using a pair of elastic members 243.

Accordingly, the contact electrodes 121 and 122 may supply current to the user's body by using power supplied from the battery 110, and thus the user's skin and the two contact electrodes 121 and 122 may form a closed circuit together.

To this end, the elastic members 243 may be formed of a material having electrical conductivity and elasticity.

In detail, each of the elastic members 243 may include a first portion 243*a* mounted on the circuit board 242, and a second portion 243*b* inclined at a certain angle from an end portion of the first portion 243*a*, and may be provided between the circuit board 242 and the contact electrodes 121 and 122 such that at least a portion of the second portion 243*b* may be in contact with bottom surfaces of the contact electrodes 121 and 122.

Thus, when the frame part 220, on which the circuit board 242 is fixed on, is fixed to the cap part 230 and then the cap part 230 and the case part 210 are coupled to each other, a close contact between the second portion 243*b* and the contact electrodes 121 and 122 corresponding to each other may be maintained. Accordingly, electricity may be conducted between the two contact electrodes 121 and 122 via the circuit board 242 fixed on the frame part 220 and the elastic members 243.

That is, in the skin care device 1000, the two contact electrodes 121 and 122 and the circuit board 242 are electrically connected to each other by being brought in close contact with each other via the elastic members 243 and thus an additional wire connection work or wiring work for connecting the circuit board 242 and the two contact electrodes 121 and 122 is unnecessary, thereby simplifying the work process and improving assemblability.

Here, a long through hole 215 may be formed in the seating plane 214 to pass through the seating plane 214 such that the second portion 243*b* of the elastic member 243 may pass through the long through hole 215 and then be pressed against the contact electrodes 121 and 122. In addition, although the elastic member 243 is illustrated as having a linear shape in the drawings, the elastic member 243 is not limited thereto and may be provided to have a certain width so as to increase a contact area thereof.

At least one protruding rib 216 may inwardly protrude from an inner side surface of the body 211 in a direction of the height of the body 211. A side of the circuit board 242 fixed on the top plate frame 221 of the frame part 220 may be pressurized by the protruding rib 216 when the cap part 230 and the case part 210 are coupled to each other, thereby aligning the circuit board 242 directly below the translucent member 212.

Thus, when a plurality of light sources 300 are mounted on the circuit board 242, an imaginary central line on the circuit board 242 may be located directly below an imaginary central line on the translucent member 212 during the assembly of the cap part 230 and the case part 210.

Accordingly, even when the light sources 300 are spaced a certain distance from a bottom surface of the translucent member 212, light generated from each of the light sources 300 may be emitted at an initially designed emission angle to the outside.

For example, the protruding rib 216 may be provided such that an inwardly protruding thickness thereof increases from bottom to top in the direction of the height of the body 211 and thus the side of the circuit board 242 may be gradually pressurized during the insertion of the frame part 220 fastened with the cap part 230 into the inner space.

The cap part 230 is configured to close a side of the inner space of the case part 210.

The cap part 230 may be integrally formed with the case part 210 but may be detachably coupled to the case part 210.

For example, a plurality of hook parts 233 may be formed at a certain height along edges of the cap part 230 to be fastened with the body 211, and stepped fastening grooves 217 may be formed at locations on the inner side surface of the body 211 corresponding to the hook parts 233 such that end portions of the hook parts 233 may be hooked by the stepped fastening grooves 217 when inserted into the stepped fastening grooves 217.

Thus, when the cap part 230 and the body 211 are coupled to each other, the end portions of the hook parts 233 may be inserted into and hooked by the fastening groove 217, thereby preventing separation of the cap part 230 and the body 211.

Accordingly, all the components of the skin care device 1000 may be assembled together by manufacturing the case part 210 by integrally forming the translucent member 212, the contact electrodes 121 and 122, and the body 211, inserting the frame parts 220 fastened with various components into the inner space of the case part 210, and fastening the cap part 230 with the body 211.

Here, at least one fastening hole 234 may be formed in the cap part 230 to pass through the cap part 230, through which a fastening member such as a bolt member may pass to increase a coupling force between the cap part 230 and the case part 210, thereby fastening the cap part 230 with the case part 210 via the fastening member.

Furthermore, the frame part 220 fixing the circuit board 242 having the light source 300 mounted thereon may be detachably coupled to the cap part 230.

For example, in the cap part 230, the coupling hole 231 is formed at the location on the cap part 230 corresponding to the coupling piece 223 to pass through the cap part 230 so that the cut piece 224 at one end of the frame part 220 may be hooked by the edge of the coupling hole 231 when coupled to the cap part 230 by being elastically deformed by an external force, inserted into the coupling hole 231, and then returning to its original state.

Furthermore, the hooking groove 232 may be formed to the certain depth in the bottom surface of the cap part 230 to be connected with the coupling hole 231 and thus the cut piece 224 may be exposed via the hooking groove 232. Thus, when the cap part 230 and the frame part 220 need to be reassembled or separated from each other, the cut piece 224 exposed via the hooking groove 232 may be pressurized by a tool such as a driver to allow the cut piece 224 to pass through the coupling hole 231, thereby separating the cap part 230 and the frame part 220 from each other.

The cap part 230 may fix not only the main circuit board 244 of the control unit 130 but also a circuit board 144 of the switch unit 140 configured to sense a manipulation signal from a user.

Here, the battery 110 may be provided on a surface of the main circuit board 244, and the battery 110, the main circuit board 244, the circuit board 242 having the light source 300 mounted thereon, and the circuit board 144 of the switch unit 140 may be electrically connected to each other.

In detail, at least one fixing rib 235 for fixing the main circuit board 244 may be formed on the cap part 230 to have a certain height.

That is, a pair of fixing ribs 235 may be provided on the top surface of the cap part 230 to be spaced a certain distance from each other, and the main circuit board 244 may be fixed on the pair of fixing ribs 235 via a fastening member such as a bolt member.

Here, the battery 110 may be disposed directly below a top plate frame 221 and between the pair of support frames 222 when the frame part 220 and the cap part 230 are coupled to each other.

That is, when the cap part 230 and the frame part 220 are coupled to each other, the battery 110 may be disposed such that a surface thereof is in contact with the main circuit board 244, a top end thereof is in contact with the protruding bar 226, and a bottom end thereof is in contact with the top surface of the cap part 230.

In this case, a cushion member 249 having a certain area may be disposed between the support frame 222 and the battery 110 to be in contact with the battery 110 and the support frame 222, thereby preventing movement of the battery 110 and absorbing external impacts. Furthermore, another cushion member may be additionally provided between the bottom surface of the battery 110 and the top surface of the cap part 230.

At least one support rib 236 having a certain height may be formed on the cap part 230 to support the circuit board 144 of the switch unit 140 configured to sense a manipulation signal from a user.

For example, a pair of support ribs 236 may be provided on the top surface of the cap part 230 to be spaced a certain distance from each other, and guide grooves 237 may be formed at the pair of support ribs 236 by cutting upper ends of the pair of support ribs 236 in a direction of height of the pair of support ribs 235 such that both sides of the circuit board 144 may be inserted into the pair of support ribs 236.

As described above, in the skin care device 1000, all of the frame part 220, the battery 110, which is a power source, the main circuit board 244, the circuit board 144 of the switch unit 140, etc. are fastened with the cap part 230, thereby simplifying an assembling process.

That is, the assembly of the skin care device 1000 may be completed by fastening the cap part 230 and the case part 210 with each other in a state in which all of the frame part 220, the battery 110, the main circuit board 244, and the circuit board 144 of the switch unit 140 are coupled to the cap part 230.

Here, a separate finishing member 238 may be attached to the bottom surface of the cap part 230 to prevent the coupling hole 231 and the hooking groove 232 from being exposed to the outside.

The light source 300 may generate light having a certain wavelength band and emit the light toward the user's skin, thereby allowing the user to obtain a unique advantageous effect from the wavelength band of the light.

In this case, the skin care device 1000 may be configured to allow unique effects from different wavelength bands to be obtained through one device.

To this end, the light source 300 may be configured to emit light having different wavelength bands. For example, a plurality of light sources 300 may be provided to emit light having different wavelength bands, but one light source 300 may be integrally formed with a plurality of light-emitting elements 331, 332, and 333 emitting light having different wavelength bands (see FIGS. 5 and 15).

That is, the light source 300 may be embodied as one package in which a plurality of light-emitting elements emitting light having different wavelength bands are mounted on one substrate. For example, the light source 300 may be a light-emitting diode (LED) used as a light-emitting element or one LED package in which a plurality of LEDs emitting light having different wavelength bands are used as a plurality of light-emitting elements.

In detail, the plurality of the light-emitting elements may include a first light-emitting element 331 emitting light having a wavelength band of 400 to 480 nm, a second light-emitting element 332 emitting light having a wavelength band of 550 to 610 nm, and a third light-emitting element 333 emitting light having a wavelength band of 610 to 650 nm.

Thus, the user may obtain effects such as soothing the skin, improving skin texture, soothing sensitive skin, improving skin contour, improving skin elasticity, restoring skin elasticity, skin lifting, moistening the skin, etc., through one light source by selecting and operating one of the first light-emitting element 331, the second light-emitting element 332, and the third light-emitting element 333 of the light source 300.

Figure 15:
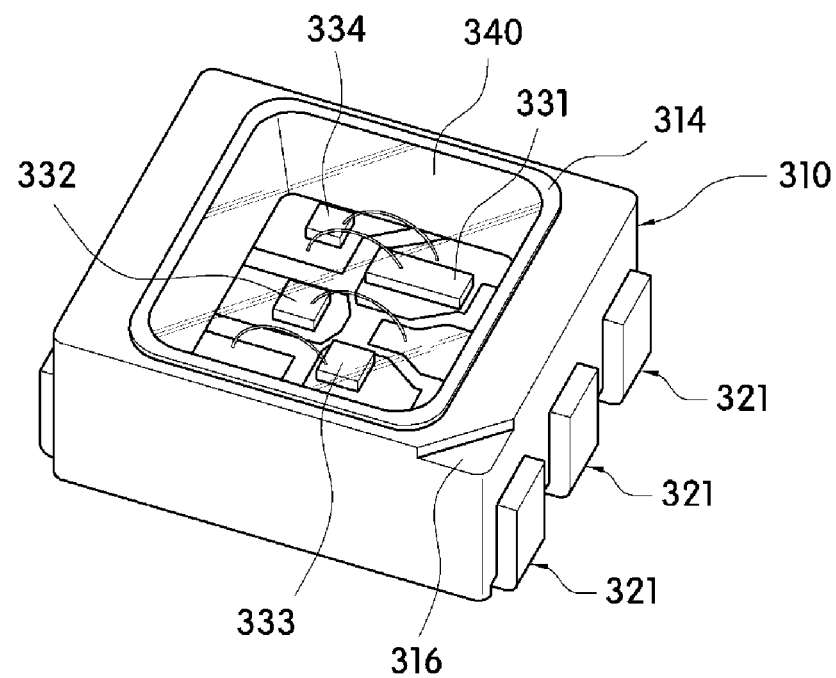
FIG. 15 is a schematic view of a light source applicable to a skin care device according to an embodiment of the present invention.
Figure 15:
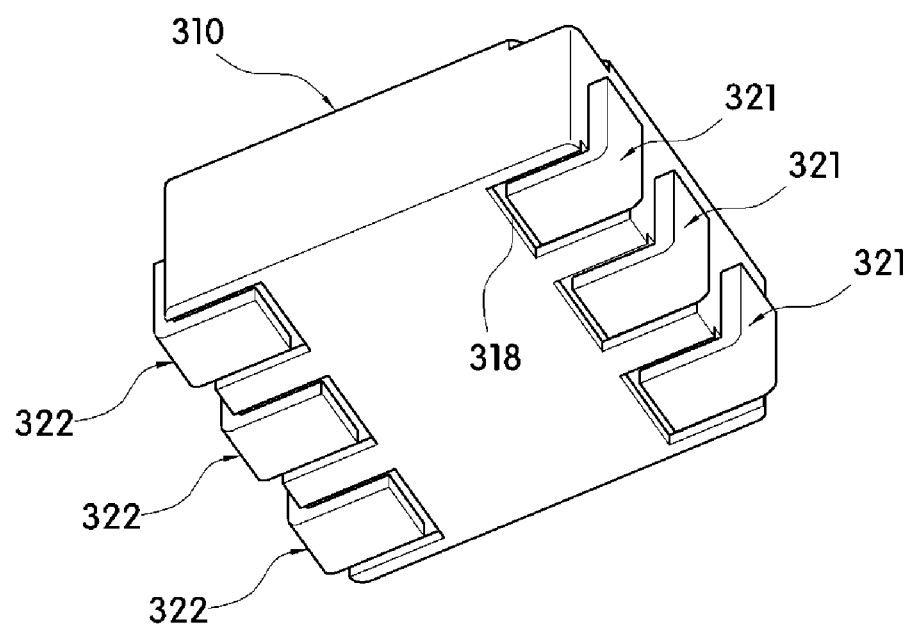
Figure 16:
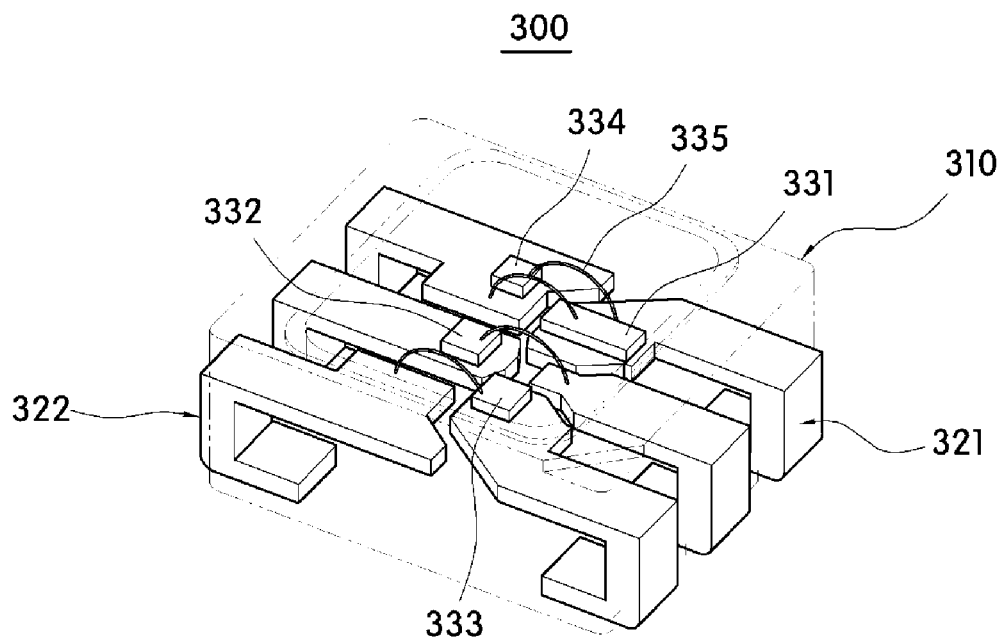
FIG. 16 is a schematic view illustrating an arrangement relationship between a plurality of electrodes and a mold body of FIG. 15.
Figure 17:
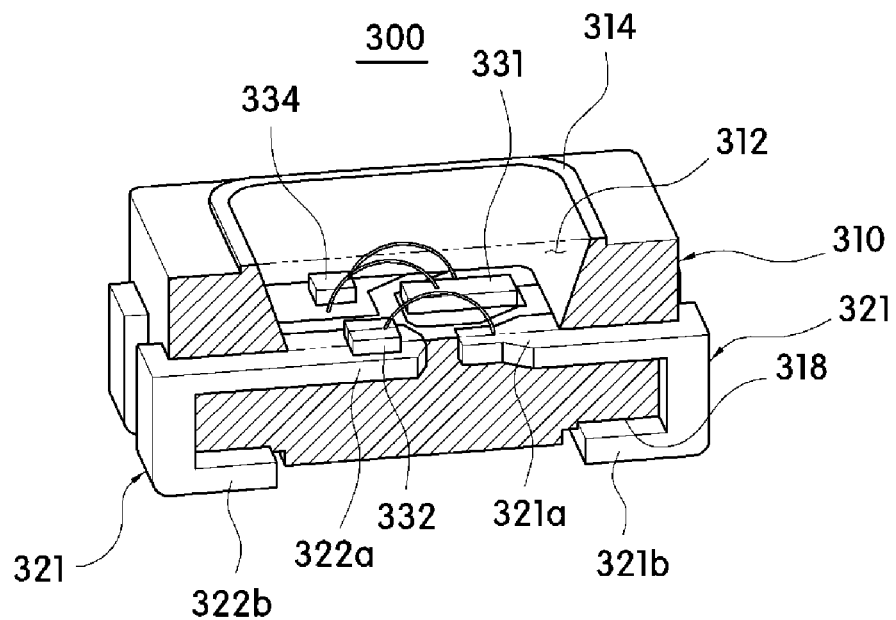
FIG. 17 is a partial sectional view of FIG. 15.
Figure 18:
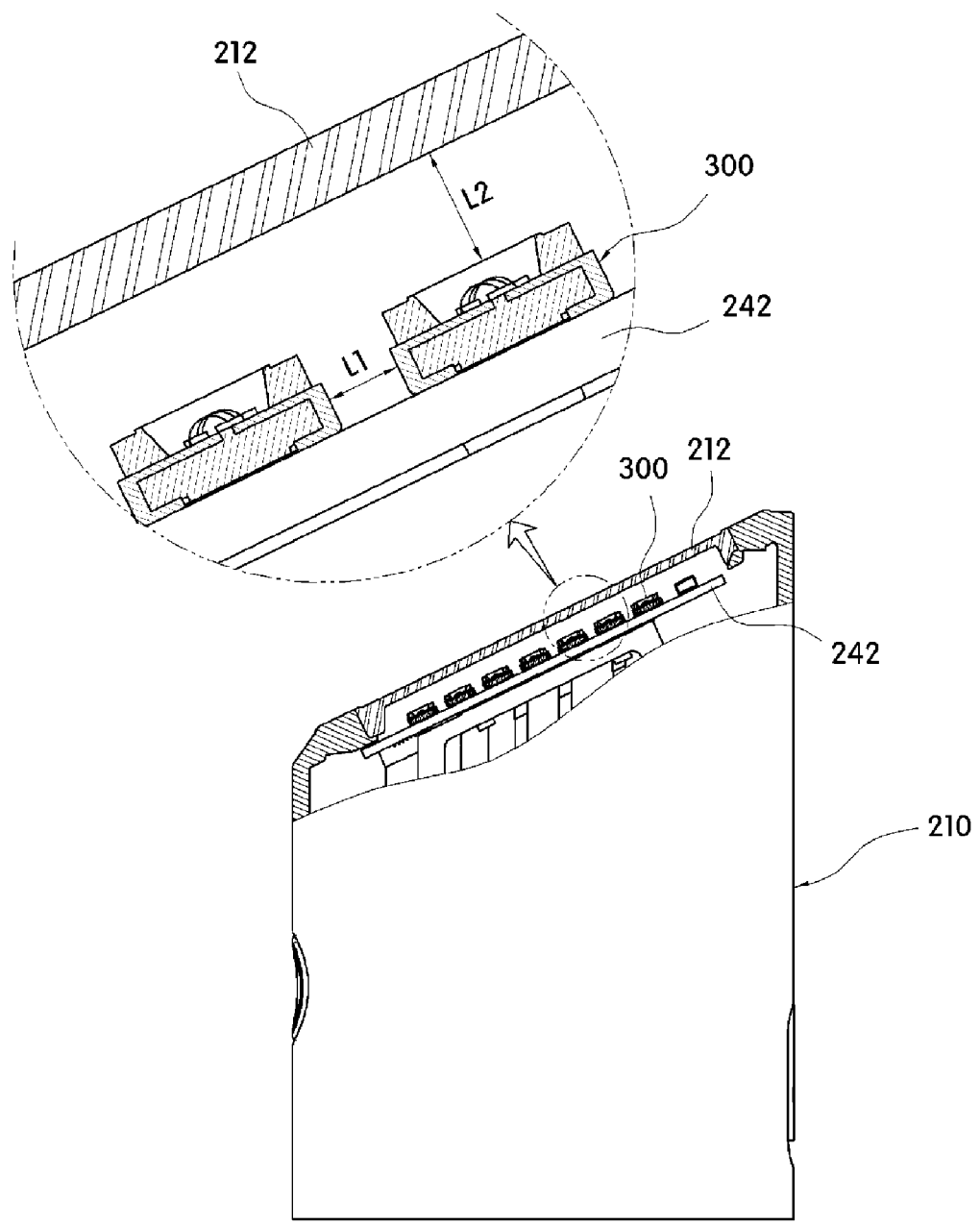
FIG. 18 is a partial cutaway view of FIG. 4.
Figure 19:
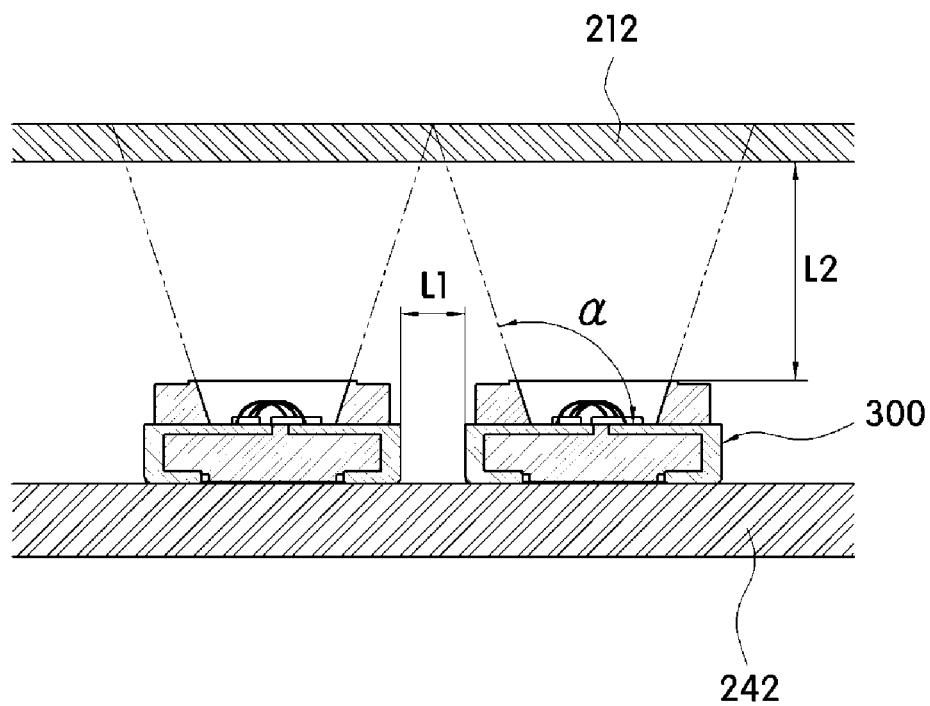
FIG. 19 is a conceptual view illustrating a separation relationship between a light source and a translucent member applicable to a skin care device according to the present invention.

To this end, the light source 300 may include a mold body 310, a plurality of connection electrodes 321 and 322, a plurality of light-emitting elements 331, 332, and 333, and an encapsulant 340 as illustrated in FIGS. 15 to 17.

The mold body 310 is configured to form a light source as one structure by molding the light-emitting elements 331, 332, and 333 and the connection electrodes 321 and 322.

That is, the light-emitting elements 331, 332, and 333 and the connection electrodes 321 and 322 may be integrally molded using a single material through the mold body 310.

Here, the mold body 310 may be formed of a mold material well known in the art. For example, the mold body 310 may be formed of silicon, a silicon oxide, various types of transparent resin, or the like.

In this case, a receiving part 312 may be formed in a top surface of the mold body 310 to a certain depth.

The receiving part 312 may provide a space for accommodating the light-emitting elements 331, 332, and 333 and may control angles of emission of light generated from the light-emitting elements 331, 332, and 333 due to an inner side surface thereof which is a surface inclined at a certain angle from top to bottom.

A reflective material having high light reflection efficiency may be applied to the inclined surface to a certain thickness so that light emitted from the light-emitting elements 331, 332, and 333 may be reflected to increase light efficiency.

The connection electrodes 321 and 322 may be electrically connected to the light-emitting elements 331, 332, and 333 to function as terminals for providing power supplied from the outside of the light source 300 to the light-emitting devices 331, 332, and 333.

That is, at least portions of the connection electrodes 321 and 322 may be exposed outside the mold body 310 and electrically connected to an electrode pattern of the circuit board 242 having the light source 300 mounted thereon so that the light-emitting elements 331, 332, and 333 may be provided with desired power.

To this end, the connection electrodes 321 and 322 may include the first electrode 321 and the second electrode 322 to which power of different polarities are supplied and may be integrated with the mold body 310 such that portions thereof are exposed to the outside.

Here, the first electrode 321 and the second electrode 322 may be formed of conductive members having a certain length, parts of which are exposed on a bottom surface of the receiving part 312 and parts of which are exposed outside the mold body 310.

That is, as illustrated in FIGS. 16 and 17, the first electrode 321 and the second electrode 322 may be formed in a roughly '⊏' shape to be integrated with the mold body 310 such that portions thereof are respectively exposed on the bottom surface of the receiving part 312 and an outer surface of the mold body 310.

Accordingly, the first electrode 321 and second electrode 322 may be electrically connected to the light-emitting elements 331, 332, and 333 via first portions 321$a$ and 322$a$ thereof exposed on the bottom surface of the receiving part 312 and may be electrically connected to the circuit board 242 via second portions 321$b$ and 322$b$ thereof exposed outside the mold body 310.

Here, although in the drawings, the second portions 321$b$ and 322$b$ of the conductive members used to form the first electrode 321 and second electrode 322 are illustrated as being exposed on both the side surface and a bottom surface of the mold body 310, the present invention is not limited thereto, and the second portions 321$b$ and 322$b$ may be exposed only on the bottom surface or the side surface of the mold body 310.

In this case, the light source 300 may include a plurality of first electrodes 321 and a plurality of second electrodes 322 to which power of different polarities are supplied. The number of the first electrodes 321 and the number of the second electrodes 322 may be the same such that they match each other one to one.

Accordingly, pluralities of light-emitting elements 331, 332, and 333 having different properties (e.g., different wavelengths) may be included in one light source 300 and thus various desired properties may be implemented by the one light source 300, as will be described in detail below.

Here, when a plurality of the first electrodes 321 and the second electrodes 322 are provided, they may be disposed such that the second portions 321$b$ and 322$b$ thereof are exposed on different surfaces of the mold body 310, and the first portions 321$a$ and 322$a$ thereof on the bottom surface of the receiving part 312 may have the same shape or different shapes.

For example, the second portions 321$b$ of the first electrodes 321 may be disposed on the right side surface and the bottom surface of the mold body 310, and the second portions 322$b$ of the second electrodes 322 may be disposed on the left side surface and the bottom surface of the mold body 310.

Accordingly, the positions of the first and second electrodes 321 and 322 to which power of different polarities are supplied may be clearly distinguished from each other, and thus, inappropriate connection of the polarities thereof by an operator during the mounting of the light source 300 on the circuit board 242 may be prevented.

In this case, at least one mark part 316 may be provided on the top surface of the mold body 310 so that the operator may more easily distinguish the polarities of the first electrode 321 and second electrode 322 from each other. For example, the mark part 316 may be a cut part formed by cutting a corner of the mold body 310. However, the mark part 316 is not limited thereto, and a color, an indication line label, or the like may be used, provided that it can be easily identified by the operator.

A seating groove 318 may be formed in the bottom surface of the mold body 310 to a certain depth, and parts of the second portions 321b and 322b may be disposed in the seating groove 318.

The light-emitting elements 331, 332, and 333 may serve as light-emitting sources for generating light of a certain wavelength band when power is supplied thereto. That is, the light-emitting elements 331, 332, and 333 may generate light of a certain wavelength band to improve the user's skin. Here, the light-emitting elements 331, 332, and 333 may generate light of a wavelength band selected within a band of 400 to 970 nm.

In this case, a total number of the light-emitting elements 331, 332, and 333 generating light having different wavelength bands may be three, and each of the light-emitting elements 331, 332, and 333 may be individually and directly mounted on one of the first and second electrodes 321 and 322 and may be connected to the other first or second electrode 321 or 322 forming a pair of the first or second electrode via a wire 335.

That is, each of the light-emitting elements 331, 332, and 333 may be electrically connected to the first or second electrode 321 or 322 by being directly mounted on the first portions 321a and 322a of one of the first and second electrodes 321 and 322 exposed on the bottom surface of the receiving part 312 and may be electrically connected to the first portions 321a and 322a of the other first or second electrode 321 or 322 forming a pair of the first or second electrode 321 or 322 the via the wire 335.

Accordingly, one of the light-emitting elements 331, 332, and 333 may be selectively operated during the supply of power and thus light of the user's desired wavelength band may be selectively emitted.

For example, the light-emitting elements 331, 332, and 333 may include the first light-emitting element 331 emitting light of a wavelength within a band of 400 to 480 nm, the second light-emitting element 332 emitting light of a wavelength within a band of 550 to 610 nm, and the third light-emitting element 333 emitting light of a wavelength within a band of 610 to 650 nm.

Accordingly, the user may obtain effects such as soothing the skin, improving skin texture, soothing sensitive skin, improving skin contour, improving skin elasticity, restoring skin elasticity, lifting the skin, treating a wound, pain relief, acne treatment, moistening the skin, etc. through one light source 300 by selecting and operating one of the first light-emitting element 331, the second light-emitting element 332, and the third light-emitting element 333.

Here, the light-emitting elements 331, 332, and 333 may be horizontal light-emitting elements or vertical light-emitting elements. Furthermore, although it is illustrated in the drawings and described in the specification that the light-emitting elements 331, 332, and 333 are directly mounted on one of the first and second electrodes 321 and 322 and are electrically connected to the other first or second electrode 321 or 322 via the wire 335, the present invention is not limited thereto and any of various electrical connection structures known in the art may be employed.

Furthermore, the number of light-emitting elements and a wavelength band which are applicable to the light source 300 are not limited to those described above, and a light-emitting element appropriate for generating a wavelength for achieving a desired skin improving effect may be used. Alternatively, each of these light-emitting elements may emit light having different wavelength bands selected within a band of 400 to 970 nm, and two light-emitting elements generating light having different wavelength bands may be configured to emit light having wavelength bands, some of which overlap each other.

A protective element 334 may be mounted on one of the first electrode 321 and the second electrode 322 to protect the light-emitting elements 331, 332, and 333 from static electricity. Similar to the light-emitting elements 331, 332, and 333, the protective element 334 may be mounted directly on the first portion 322a exposed on the bottom surface of the receiving part 312 and may be electrically connected to the first portion 321a of the other first or second electrode 321 or 322 forming a pair of the first or second electrode 321 or 322 via the wire 335. A well-known Zener diode may be used as an example of the protective element 334. However, the protective element 334 is not limited thereto, and any other devices are available provided that they can protect a circuit from static electricity.

In this case, the light-emitting elements 331, 332, and 333 emitting light having different wavelength bands may be set to emit different amounts of light according to a wavelength band to be used.

For example, the light-emitting element 331 having a wavelength of less than 500 nm among the light-emitting elements 331, 332, and 333 may be set to emit a smaller amount of light than the amounts of light to be emitted from light-emitting elements 332 and 333 each having a wavelength band of 500 nm or more.

In detail, the speed of light from a light-emitting element having a wavelength band of less than 500 nm may be 6 lumens or less, and the speed of light from a light-emitting element having a wavelength band of 500 nm or more may be 8 lumens or less.

That is, the first light-emitting element 331 emitting light having a wavelength band of 400 to 480 nm may emit light at a luminous flux of 6 lumens or less, the second light-emitting element 332 emitting light having a wavelength band of 550 to 610 nm wavelength band, and the third light-emitting element 333 emitting light having a wavelength band of 610 to 650 nm may emit light at a luminous flux of 8 lumens or less.

The first light-emitting element 331 having a relatively short wavelength generates heat higher than those generated by the second and third light-emitting elements 332 and 333 having relatively longer wavelengths. This is to prevent a user from feeling discomfort due to heat generated by the light-emitting elements 331, 332, and 333 and prevent a harmful effect to the user, e.g., damage to his or her eyes, by the generated light during the contact of the user's body with the skin care device 1000 when the light source 300 is applied to the skin care device 1000 configured to be in contact with the user's body.

That is, in the present invention, the speed of light emitted from each of the light-emitting elements 331, 332, and 333 may be controlled by the control unit 130 to be 8 lumens or 6 lumens or less according to the wavelength band thereof so that the light-emitting elements 331, 332, and 333 may emit light having a temperature of 40° C. or less which is similar to the temperature of a human body.

The encapsulant 340 may be a resin material filling in the receiving part 312 to cover and protect the light-emitting elements 331, 332, and 333 and the wire 335 disposed on the receiving part 312.

The encapsulant 340 may be a transparent resin to directly transmit the color of light generated from the light-emitting elements 331, 332, and 333 disposed in the receiving part 312, or may be a transparent resin containing a fluorescent substance to change wavelengths of light generated by the light-emitting elements 331, 332, and 333 and emit light having a different color.

In this case, a protrusion part 314 may protrude a certain height from the top surface of the mold body 310 along an edge of the receiving part 312. The protrusion part 314 is configured to prevent the encapsulant 340 filling in the receiving part 312 from overflowing or being lost via an open upper portion of the receiving part 312 during a curing process when the light source 300 is manufactured.

However, the type of the light source is not limited thereto, and any light source capable of emitting a wavelength appropriate to improve the skin is available.

For example, the light-emitting elements 331, 332, and 333 may emit light having different wavelength bands selected within a wavelength band of 400 to 970 nm, and two different light-emitting elements may be configured to emit light having wavelength bands, some of which overlap with each other.

Alternatively, the light source may include one light-emitting element emitting light having a certain wavelength band within a band of 400 to 970 nm. In this case, two or more light sources as the light source may be appropriately used to emit light having different wavelength bands.

In addition, the light source may be continuously turned on or may be repeatedly turned on and off.

When the light source 300 includes a plurality of light-emitting elements emitting light having different wavelength bands, an emission mode of the light source 300 may be selected through manipulation of the switch unit 140 provided at one side of the case part 210, and driving of the light source 130 may be controlled by the control unit 130.

Here, as illustrated in FIG. 4, the switch unit 140 may include the at least one button 142 exposed at one side of the case part 210 and the circuit board 144 included in the case part 210 and having a circuit part generating a signal corresponding to manipulation of the button 142. The circuit board 144 may be electrically connected to a main circuit board 134 of the control unit 130.

For example, the switch unit 140 may be a well-known tact switch, and may be sequentially switched to a first emission mode, a second emission mode, and a third emission mode by driving the control unit 130 according to a number of times the button 142 pressed by a user or may be sequentially switched to the strong mode, the normal mode, and the weak mode. However, the present invention is not limited thereto, and the button 142 may be manipulated to select an emission mode and an intensity mode of a light source or to turn on or off a skin care device.

Furthermore, the control unit 130 may have a timer function to block the supply of power to the light-emitting elements 331, 332, and 333 at a predetermined time after the light-emitting elements 331, 332, and 333 are continuously operated.

The light source 300 may be mounted in a certain pattern on the circuit board 242 fixed on the top plate frame 221 of the frame part 220 and may be disposed below the translucent member 212 during the coupling of the cap part 230 and the case part 210.

In this case, the light source 300 may be disposed such that a side thereof is in contact with the translucent member 212 and the light source 300 is spaced a certain distance from a surface of the translucent member 212. Furthermore, when a plurality of light sources 300 are provided, the plurality of the light sources 300 may be spaced the same distance or different distances from the translucent member 212.

In detail, when a plurality of light sources 300 are provided and spaced a certain distance from the translucent member 212, a distance L1 between two adjacent light sources 300 and a distance L2 from each of the light sources 300 to the translucent member 212 may satisfy Equation 1 below.

$$L2/L1 \leq 1.6 \qquad \text{[Equation 1]}$$

This is because when the distance from each of the light sources 300 to the translucent member 212 is 1.6 times or less the distance from each of adjacent light sources 300 to the translucent member 212, lights emitted from the light sources 300 and reaching the translucent member 212 don't overlap with each other, thereby preventing attenuation or loss of the light due to the overlapping thereof.

Accordingly, a decrease in the amount of light generated from each of the light sources 300 may be prevented and thus a beneficial effect which a user desires to obtain from a certain wavelength band may be obtained. In addition, light may be emitted at a luminous flux of 8 lumens or less and thus problems caused by heat generation may be solved.

As described above, in the skin care device 1000, the distance between the light sources 300 and the distance between the light source 300 and the translucent member 212 are limited to be within predetermined ranges and thus the light-emitting elements 331, 332, and 333 emitting light having different wavelength bands may be simultaneously used and ideal light distribution may be achieved even when a plurality of light sources 300 are disposed.

When the light source 300 and the translucent member 212 are disposed spaced a certain distance from each other through the coupling of the cap part 230 and the case part 210, the light source 300 may be disposed directly below an area corresponding to the translucent member 212. Thus, in the skin care device 1000 according to the present invention, the light source 300 generating light is disposed below the translucent member 212 to be spaced a certain distance from the translucent member 212 in a state in which the light source 300 is accommodated in the case part 210 and thus an angle of emission of light emitted outside may be limited.

That is, an angle of emission of light emitted from the light source 300 via the translucent member 212 disposed in the hollow portion of the seating plane 214 may be relatively narrower than that of emission of light of the light source 300 itself.

Accordingly, even when the light source 300 is operated close to the user's skin, and particularly, the user's face, light generated from the light source 300 may be emitted at a narrow range to the user's skin to be cared for, thereby preventing the light from entering the user's eyes.

In this case, the light source 300 may be turned on only when the distance between the light source 300 and the skin is within a predetermined range and turned off when the distance between the light source 300 and the skin is beyond the predetermined range.

This is to prevent the user's eyes from being directly exposed to the light emitted from the light source 300 when the translucent member 212 is inadvertently positioned toward the user's eyes during use, thereby preventing damage to the user's eyes.

To this end, at least one proximity sensor 246 may be provided on the circuit board 242 having the light source 300 mounted thereon to control the turning on or off of the light source 300 by sensing the distance between the light source 300 and the skin.

Here, a plurality of proximity sensors 246 may be provided and the proximity sensors 246 may be disposed between adjacent light sources 300 or an outer side of an outermost light source 300.

Furthermore, initial turning-on of the light source 300 may be performed only when both of the two contact electrodes 121 and 122 are in contact with the user's skin and when the distance between the light source 300 and the user's skin is within a predetermined range.

This is to control initial lighting by sensing whether contact electrodes is in contact with the user's skin even when the distance between the light source 300 and the user's skin is short and is within the predetermined range during movement to the user's body part to be cared for so that initial lighting may be performed when finally moved to an exact location on the user's skin that the user desires to be cared for. Accordingly, the light source 300 may be prevented from suddenly operating regardless of the user's intention.

The translucent member 212 may be integrally formed with the body 211 and located in front of the light source 300 to protect the light source 300 from an external environment and protect the user's eyes from light emitted outside when the light source 300 is turned on. Furthermore, the translucent member 212 may perform a function of increasing the diffusion of light generated from the light source 300 to uniformly emit light outside.

To this end, the translucent member 212 may be provided having a certain transmittance to reduce the intensity of light generated from the light source 300 and emitted outside and may include a light diffusing substance to uniformly emit light outside.

For example, the translucent member 212 may have a transmittance of 70 to 90% and preferably may be formed of light diffusion polycarbonate (PC) having a transmittance of 70 to 90%. Here, it is described that the transmittance of the translucent member 212 is 70 to 90% but is not limited thereto and may be appropriately adjusted provided that the diffusion of light can be increased while the user's eyes can be protected.

The body 211 may include a light blocking material to prevent light emitted from the light source 300 from being emitted outside via the body 211. Here, the light blocking material may be a well-known black resin or a black pigment but is not limited thereto and any other materials capable of blocking light and preventing light leakage are available. In addition, the body 211 may include a metal material, such as chromium (Cr), gold (Au), silver (Ag), copper (Cu), or platinum (Pt), so that both an effect of blocking electromagnetic waves and an effect of blocking light may be achieved.

The skin care device 1000 may include a control unit to control overall operations thereof by changing an emission mode of the light source 300 through manipulation of the button 142, supplying power or blocking the supply of power, turning the light source 300 on or off, and processing information obtained by the proximity sensor 246.

The control unit may be the control unit 130 of the above-described iontophoresis device 100, to which functions of changing an emission mode of the light source 300 through manipulation of the button 142, supplying power or blocking the supply of power, and turning the light source 300 on or off, a function of processing information obtained by the proximity sensor 246, a timer function, etc. are added.

Furthermore, the control unit may include a lookup table for controlling an operating state of and an intensity of an output of the light source 300 according to the distance between the skin and the light source 300 obtained by the proximity sensor 246 and for appropriately adjusting a direct current to be supplied to the contact electrodes 121 and 122.

The skin care device 1000 may further include a notification unit configured to be connected with the manipulation of the button 142. When the button 142 is manipulated by a user, the notification unit is controlled to be driven by the control unit and thus the user may easily identify whether the button 142 is manipulated or not. For example, the notification unit may be a vibration unit 247 electrically connected to the circuit board 242 or an audio output unit (not shown), such as a speaker, which outputs sound to the outside. Here, the vibration unit 247 may be a vibration motor or a vibration sensor.

That is, when the button 142 is pressed by the user, the control unit may generate vibration via the vibration unit 247 or may output sound to the outside by identifying the manipulation of the button 142 and driving the notification unit on the basis of a signal transmitted from the circuit board 144 behind the button 142. Accordingly, the user may easily identify whether power is turned on or off and whether an emission mode of the light source 300 is changed and thus may accurately switch to a desired emission mode through manipulation of the button 142.

Here, an output pattern of the notification unit may vary according to an emission mode. For example, in the case of a vibration pattern generated by the vibration unit 247, at least one of the intensity of vibration and a duration of vibration may be output in a different pattern when a first emission mode, a second emission mode, or a third emission mode is selected and switched to, and unique sound may be output outside for each mode when sound is output via a speaker.

The skin care device 1000 may include a cover 250 detachably coupled to the case part 210 so as to protect the two contact electrodes 121 and 122 and the translucent member 212 located on the case part 210 to be exposed outside from an external environment.

The skin care device 1000 may further include a charging terminal 248 provided at one side of the case part 210 and exposed outside, and thus, the battery included in the case part 210 may be conveniently charged.

Here, the charging terminal 248 may be electrically connected to the main circuit board 244 and thus the battery may be charged with power supplied from the outside.

Although it is described above that the iontophoresis device 100 according to the present invention is applied to the above-described skin care device 1000, the structure of the skin care device 1000 is not limited thereto and the iontophoresis device 100 may be appropriately employed in various types of well-known skin care devices capable of employing having the light source 300.

Furthermore, the two contact electrodes 121 and 122 of the iontophoresis device 100 may be embodied as bipolar contact electrodes disposed on the same surface of the case part 210 to be spaced from each other or may be disposed at different positions.

In addition, the light source 300 mentioned in the above-described embodiment may be appropriately employed in various types of well-known skin care devices, as well as the skin care device 1000. Alternatively, the light source 300 alone may be employed in well-known skin care devices having no iontophoresis function.

While embodiments of the present invention have been described above, the scope of the present invention is not limited thereto, and other embodiments may be easily suggested by those of ordinary skill in the art by adding or changing components without departing from the scope of the invention. The other embodiments should be understood to fall within the scope of the present invention.

The invention claimed is:

1. An iontophoresis device comprising:
   a case part configured to provide a seating plane formed along an upper edge of the case part; wherein a bottom of the case part is open;
   a power supply unit configured to supply power;
   two electrodes configured to be disposed on the seating plane; wherein the two electrodes are configured to supply current to a user's skin when brought into contact with the user's skin, thereby allowing an ionic drug or an active ingredient applied to the user's skin to permeate the user's skin by an electrical repulsive force;
   a control unit configured to adjust an output value of a voltage or a current applied to the two electrodes according to a condition of the user's skin, thereby allowing the user to feel a uniform intensity of electrical stimulation;
   a frame part configured to be provided in an inner space of the case part;
   a circuit board configured to be fixed onto the frame part;
   two elastic members configured to be formed of a material having electrical conductivity; wherein the two elastic members are configured to be disposed between the circuit board and the two electrodes; and
   a cap part configured to detachably couple to the bottom of the case part in a state coupled to the frame part,
   wherein the two electrodes are electrically connected to the circuit board via the two elastic members,
   wherein the two elastic members include a first portion mounted on the circuit board, and a second portion inclined at an angle from an end portion of the first portion,
   wherein a part of the second portion is in contact with bottom surfaces of the two electrodes when the cap portion is coupled to the case part,
   wherein the seating plane is an inclined plane with a certain slope for the two electrodes disposed thereon to incline with respect to the bottom of the case part.

2. The iontophoresis device of claim 1, wherein the control unit comprises:
   a sensing part configured to identify whether the two electrodes and the user's skin are in contact with each other and measure the user's skin condition;
   an integrated control part configured to identify the user's skin condition measured by the sensing part and control overall operations of the iontophoresis device; and
   an output generating part configured to change the output value according to a signal output from the integrated control part based on the user's skin condition.

3. The iontophoresis device of claim 2, wherein the output generating part adjusts the output value based on an amount of change in the voltage or the current changed according to at least one among a moisture content of a surface of the user's skin, a thickness of the user's skin, whether the ionic drug or the active ingredient is applied or not, and a thickness of the ionic drug or active ingredient after application.

4. The iontophoresis device of claim 3, wherein the adjustment of the output value is performed by changing one of the voltage, the current, and a duty ratio of a pulse current applied to the two electrodes.

5. The iontophoresis device of claim 2, wherein the control unit determines that the two electrodes and the user's skin are in contact with each other when an amount of change in the voltage or the current measured by the sensing part during the supply of power is greater than or equal to a predetermined level and outputs, via the output generating part, an output value having a certain range and being stored in a lookup table.

6. The iontophoresis device of claim 5, wherein the output value output via the output generating part matches the amount of change in the voltage or the current measured by the sensing part in a one to one manner.

7. The iontophoresis device of claim 5, wherein a voltage applied to the two electrodes to determine whether the two electrodes and the user's skin are in contact with each other is lower than that applied to the two electrodes to allow the ionic drug or the active ingredient applied to the user's skin to permeate the user's skin.

8. The iontophoresis device of claim 1, further comprising a switch unit configured to be capable of being manipulated by the user,
   wherein the control unit is changed to a plurality of output modes having output values of different ranges during manipulation of the switch unit.

9. A skin care device comprising:
   an iontophoresis device; and
   at least one light source configured to generate light having a certain wavelength band and emit the light toward a user's skin,
   wherein the iontophoresis device comprises:
   a case part configured to provide a seating plane formed along an upper edge of the case part; wherein a bottom of the case part is open;
   a power supply unit configured to supply power;
   two electrodes configured to be disposed on the seating plane; wherein the two electrodes configured to supply current to the user's skin when brought into contact with the user's skin, thereby allowing an ionic drug or an active ingredient applied to the user's skin to permeate the user's skin by an electrical repulsive force;
   a control unit configured to adjust an output value of a voltage or a current applied to the two electrodes according to a condition of the user's skin, thereby allowing the user to feel a uniform intensity of electrical stimulation;
   a frame part configured to be provided in an inner space of the case part;
   a circuit board configured to be fixed onto the frame part;
   two elastic members configured to be formed of a material having electrical conductivity; wherein two elastic members are configured to be disposed between the circuit board and the two electrodes; and
   a cap part configured to be detachably coupled to the bottom of the case part in a state coupled to the frame part,
   wherein the two electrodes are electrically connected to the circuit board via the two elastic members,
   wherein the two elastic members include a first portion mounted on the circuit board, and a second portion inclined at a certain angle from an end portion of the first portion,
   wherein one portion of the second portion is in contact with bottom surfaces of the two electrodes when the cap portion is coupled to the case part,
   wherein the seating plane is an inclined plane with a certain slope for the two electrodes disposed thereon to incline with respect to the bottom of the case part.

10. The skin care device of claim 9, wherein the at least one light source comprises a plurality of light-emitting elements having different wavelength bands and being integrally formed with each other.

11. An iontophoresis method of supplying current to a user's skin to allow an ionic drug or an active ingredient applied to the user's skin to permeate the user's skin by an electrical repulsive force when contacting with the user's skin, the iontophoresis method comprising adjusting an output value of a voltage or a current applied to two electrodes which are in contact with the user's skin according to a condition of the user's skin to allow the user to feel a uniform intensity of electrical stimulation, wherein the two electrodes configured to be disposed on a seating plane of a case part, wherein a frame part is provided in an inner space of the case part, wherein a circuit board is fixed onto the frame part, wherein a cap part is detachably coupled to the bottom of the case part in a state coupled to the frame part, wherein the two electrodes are electrically connected to the circuit board via two elastic members having electrical conductivity when the cap is coupled to the bottom of the case part, wherein the seating plane is an inclined plane with a slope for the two electrodes to incline with respect to the bottom of the case part.

12. The iontophoresis method of claim 11, wherein the adjustment of the output value is performed based on an amount of change in the voltage or the current changed according to at least one among a moisture content of a surface of the user's skin, a thickness of the user's skin, whether the ionic drug or the active ingredient is applied or not, and a thickness of the ionic drug or active ingredient after application.

13. The iontophoresis method of claim 12, wherein the adjustment of the output value is performed by changing one of the voltage, the current, and a duty ratio of a pulse current applied to at least one of the two electrodes.

* * * * *